(12) United States Patent
Ecker et al.

(10) Patent No.: US 6,221,587 B1
(45) Date of Patent: Apr. 24, 2001

(54) IDENTIFICATION OF MOLECULAR INTERACTION SITES IN RNA FOR NOVEL DRUG DISCOVERY

(75) Inventors: David J. Ecker, Encinitas; Ranga Sampath, San Diego; Richard Griffey, Vista; John McNeil, La Jolla, all of CA (US)

(73) Assignee: ISIS Pharmceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/076,440

(22) Filed: May 12, 1998

(51) Int. Cl.⁷ .............................. C12Q 1/68; C12P 19/34
(52) U.S. Cl. ............................... 435/6; 435/91.2
(58) Field of Search ........................ 435/6, 91.2

(56) References Cited

U.S. PATENT DOCUMENTS

| | | | |
|---|---|---|---|
| 5,885,834 | 3/1999 | Epstein | 435/375 |
| 5,977,311 | 11/1999 | Nandabalan et al. | 530/358 |

OTHER PUBLICATIONS

Haynes et al. DNA Sequence 8(N1–2), 105–108 (Biosis Abstract), 1997.*

Landers et al., "Transitional Enhancement of mdm2 Oncogene Expression in Human Tumor Cells Containing a Stabilized Wild–Type p53 Protein", *Cancer Res.*, 1997, 57, 3562–3568.

Müller–Pillasch et al., "Cloning of Novel Transcripts of the Human Guanine–Nucleotide–Exchange Factor Mss4: In Siu Chromosomal Mapping and Expression in Pancreatic Cancer", *Genomics*, 1987, 46, 389–396.

Scott et al., "A Truncated Intracellular HER2/neu Receptor Produced by Alternative RNA Processing Affects Growth of Human Carcinoma Cells", *Mol. Cell Biol.*, 1993, 13(4), 2247–2257.

Addess et al., "Structure and Dynamics of the Iron Responsive Element RNA: Implications for Binding of the RNA by Iron Regulatory Binding Proteins", *J. Mol. Biol.*, 1997, 274, 72–83.

Benson et al., "GenBank", *Nucl. Acids Res.*, 1998, 26(1), 1–7.

Brown, J.W., "Phylogenetic analysis of RNA structure on the Macintosh computer", *CABIOS Commun.*, 1991, 7(3), 391–393.

Gautheret et al., "Inferring the conformation of RNA base pairs and triples from patterns of sequence variation", *Nucl. Acids Res.*, 1997, 25(8), 1559–1564.

Gautheret at al., "G · U base pairing motifs in ribosomal RNA", *RNA*, 1995, 1, 807–814.

Gautheret et al., "Identification of Base–triples in RNA using Comparative Sequence Analysis", *J. Mol. Biol.*, 1995, 248, 27–43.

Gdaniec et al., "Iron Regulatory Element and Internal Loop/Bulge Structure for Ferritin mRNA Studied by Cobalt(III) Hexammine Binding, Molecular Modeling, and NMR Spectroscopy", *Biochem.*, 1998, 37, 1505–1512.

Gutell, "Collection of small subunit (16S–and 16S–like) ribosomal RNA structures: 1994", *Nucl. Acids Res.*, 1994, 22(17), 3502–3507.

Gutell, "Collection of small subunit (16S–and 16S–like) ribosomal RNA structures", *Nucl. Acids Res.*, 1993, 21(13), 3051–3054.

Gutell, "A compilation of large subunit (23S and 23S–like) ribosomal RNA structures: 1993", *Nucl. Acids Res.*, 1993, 21(13), 3055–3074.

Gutell et al., "Comparative Sequence Analysis of Experiments Performed During Evolution", In Ribosomal RNA Group I Introns, Green (ed.), Austin: Landes, 1996.

Laferriere et al., "An RNA pattern matching program with enhanced performance and portability", *Comput. Appl. Biosci.*, 1994, 10(2), 211–212.

Lodmell et al., "Genetic and comparative analyses reveal an alternative secondary structure in the region of nt 912 *Escherichia coli* 16S rRNA", *Proc. Natl. Acad. Sci. USA*, 1995, 92, 10555–10559.

Sutton et al., "TIGR Assembler: A New Tood for Assembling Large Shotgun Sequencing Projects", *Genome Science & Tech.*, 1995, 1(1), 9–19.

Thompson et al., "CLUSTAL W: improving the sensitivity of progressive multiple sequence alignment through sequence weighting, position–specific gap penalties and weight matrix choice", *Nucl. Acids Res.*, 1994, 22(22), 4673–4680.

Woese et al., "Evidence for several higher order structural elements in ribosomal RNA", *Proc. Natl. Acad. Sci. USA*, 1989, 86, 3119–3122.

Woese et al., "Secondary structure model for bacterial 16S ribosomal RNA: phylogenetic, enzymatic and chemical evidence", *Nucl. Acids Res.*, 1980, 8(10), 2275–2293.

* cited by examiner

*Primary Examiner*—Eggerton A. Campbell
(74) *Attorney, Agent, or Firm*—Woodcock Washburn Kurtz Mackiewicz & Norris LLP

(57) ABSTRACT

Methods of identifying molecular interaction sites in eukaryotic and prokaryotic nucleic acids, especially RNA, are described. Secondary structural elements are identified from highly conserved sequences. Methods of preparing databases relating to such molecular interaction sites are also provided herein as are databases themselves. Therapeutic, agricultural, industrial, and other applicability results from interaction of such molecular interaction sites with "small" and other molecules.

21 Claims, 15 Drawing Sheets

IRE Stem-loop Model

| | HUMAN PIG | HAMSTER MOUSE RAT | CHICKEN | TROUT SALMON | XENOPUS FROG | FLY | MOSQUITO |
|---|---|---|---|---|---|---|---|
| HUMAN PIG | | No | Yes | Yes | Yes | No | No |
| HAMSTER MOUSE RAT | No | | Yes | Yes | Yes | No | No |
| CHICKEN | | | | Yes | Yes | No | No |
| TROUT SALMON | | No | No | | No | Yes | Yes |
| XENOPUS FROG | | | | | | Yes | Yes |
| FLY | | | | | | | No |
| MOSQUITO | | | | | | | |

IDENTIFICATION OF MOLECULAR INTERACTION SITES IN RNA FOR NOVEL DRUG DISCOVERY

FIELD OF THE INVENTION

The present invention is directed to methods of identifying regions of nucleic acids, especially RNA, in prokaryotes and eukaryotes that can serve as molecular interaction sites. Therapeutics and structural databases are also comprehended by the present invention.

BACKGROUND OF THE INVENTION

Recent advances in genomics, molecular biology, and structural biology have highlighted how RNA molecules participate in or control many of the events required to express proteins in cells. Rather than function as simple intermediaries, RNA molecules actively regulate their own transcription from DNA, splice and edit mRNA molecules and tRNA molecules, synthesize peptide bonds in the ribosome, catalyze the migration of nascent proteins to the cell membrane, and provide fine control over the rate of translation of messages. RNA molecules can adopt a variety of unique structural motifs, which provide the framework required to perform these functions.

"Small" molecule therapeutics, which bind specifically to structured RNA molecules, are organic chemical molecules which are not polymers. "Small" molecule therapeutics include the most powerful naturally-occurring antibiotics. For example, the aminoglycoside and macrolide antibiotics are "small" molecules that bind to defined regions in ribosomal RNA (rRNA) structures and work, it is believed, by blocking conformational changes in the RNA required for protein synthesis. Changes in the conformation of RNA molecules have been shown to regulate rates of transcription and translation of mRNA molecules.

An additional opportunity in targeting RNA for drug discovery is that cells frequently create different mRNA molecules in different tissues that can be translated into identical proteins. Processes such as alternative splicing and alternative polyadenylation can create transcripts that are unique or enriched in particular tissues. This provides the opportunity to design drugs that bind to the region of RNA unique in a desired tissue, including tumors, and not affect protein expression in other tissues, or affect protein expression to a lesser extent, providing an additional level of drug specificity generally not achieved by therapeutic targeting of proteins.

RNA molecules or groups of related RNA molecules are believed by Applicants to have regulatory regions that are used by the cell to control synthesis of proteins. The cell is believed to exercise control over both the timing and the amount of protein that is synthesized by direct, specific interactions with mRNA. This notion is inconsistent with the impression obtained by reading the scientific literature on gene regulation, which is highly focused on transcription. The process of RNA maturation, transport, intracellular localization and translation are rich in RNA recognition sites that provide good opportunities for drug binding. Applicants' invention is directed to finding these regions for RNA molecules in the human genome as well as in other animal genomes and prokaryotic genomes.

Accordingly, it is a principal object of the invention to identify molecular interaction sites in nucleic acids, especially RNA. A further object of the invention is to identify secondary structural elements in RNA which are highly likely to give rise to significant therapeutic, regulatory, or other interactions with "small" molecules and the like. Identification of tissue-enriched unique structures in RNA is another objective of the present invention.

SUMMARY OF THE INVENTION

Applicants' invention is directed to methods of identifying secondary structures in eukaryotic and prokaryotic RNA molecules termed "molecular interaction sites." Molecular interaction sites are small, usually less than 30 nucleotides, independently folded, functional subdomains contained within a larger RNA molecule. Applicants' methods preferably comprise a family of integrated processes that analyze nucleic acid, preferably RNA, sequences and predict their structure and function. Applicants' methods preferably comprise processes that execute subroutines in sequence, where the results of one process are used to trigger a specific course of action or provide numerical or other input to other steps. Preferably, there are decision points in the processes where the paths taken are determined by expert processes that make decisions without detailed, real-time human intervention. Automation of the analysis of RNA sequences provides the ability to identify regulatory sites at the rate that RNA sequences become available from genomic sequence databases and otherwise. The invention can be used, for example, to identify molecular interaction sites in connection with central nervous system (CNS) disease, metabolic disease, pain, degenerative diseases of aging, cancer, inflammatory disease, cardiovascular disease and many other conditions. Applicants' invention can also be used, for example, to identify molecular interaction sites, which are absent from eukaryotes, particularly humans, which can serves as sites for "small" molecule binding with concomitant modulation, either augmenting or diminishing, of the RNA of prokaryotic organisms. Human toxicity can, thus, be avoided in the treatment of viral, bacterial or parasitic disease.

The present invention preferably identifies molecular interaction sites in a target nucleic acid by comparing the nucleotide sequence of the target nucleic acid with the nucleotide sequences of a plurality of nucleic acids from different taxonomic species, identifying at least one sequence region which is effectively conserved among the plurality of nucleic acids and the target nucleic acid, determining whether the conserved region has secondary structure, and, for conserved regions having secondary structure, identifying the secondary structures.

The present invention is also directed to databases relating to molecular interaction sites, in eukaryotic and prokaryotic RNA. The databases are obtained by comparing the nucleotide sequence of the target nucleic acid with the nucleotide sequences of a plurality of nucleic acids from different taxonomic species, identifying at least one sequence region which is conserved among the plurality of nucleic acids and the target nucleic acid, determining whether the conserved region has secondary structure, and for the conserved regions having secondary structure, identifying the secondary structures, and compiling a group of such secondary structures.

The present invention is also directed to oligonucleotides comprising a molecular interaction site that is present in the RNA of a selected organism and in the RNA of at least one additional organism, wherein the molecular interaction site serves as a binding site for at least one molecule which, when bound to the molecular interaction site, modulates the expression of the RNA in the selected organism.

The present invention is also directed to an oligonucleotide comprising a molecular interaction site that is present in prokaryotic RNA and in at least one additional prokaryotic RNA, wherein the molecular interaction site serves as a binding site for at least one molecule, when bound to the molecular interaction site, modulates the expression of the prokaryotic RNA.

The present invention also concerns pharmaceutical compositions comprising an oligonucleotide having a molecular interaction site that is present in prokaryotic RNA and in at least one additional prokaryotic RNA, wherein the molecular interaction site serves as a binding site for at least one "small" molecule. Such molecule, when bound to the molecular interaction site, modulates the expression of the prokaryotic RNA. A pharmaceutical carrier is also preferably included.

The present invention also provides pharmaceutical compositions comprising an oligonucleotide comprising a molecular interaction site that is present in the RNA of a selected organism and in the RNA of at least one additional organism. The molecular interaction site serves as a binding site for at least one molecule that, when bound to the molecular interaction site, modulates the expression of the RNA in the selected organism, and a pharmaceutical carrier.

Ultimately, the methods of the present invention identify the physical structures present in a target nucleic acid which are of great importance to an organism in which the nucleic acid is present. Such structures—called molecular interaction sites—are capable of interacting with molecular species to modify the nature or effect of the nucleic acid. This may be exploited therapeutically as will be appreciated by persons skilled in the art. Such structures may also be found in the nucleic acid of organisms having great importance in agriculture, pollution control, industrial biochemistry, and otherwise. Accordingly, pesticides, herbicides, fungicides, industrial organisms such as yeast, bacteria, viruses, and the like, and biocatalytic systems may be benefitted hereby.

While there are a number of ways to characterize binding between molecular interaction sites and ligands, such as for example, organic compounds, preferred methodologies are described in U.S. patent applications filed on even date herewith and assigned to the assignee of this invention. These application bear U.S. Ser. Nos. 09/076,405, 09/076,447, 09/076,206, 09/076,214 and 09/076,404. All of the foregoing applications are incorporated by reference herein in their entirety.

BRIEF DESCRIPTION OF THE DRAWINGS

FIG. 13 shows a representative lookup table used in Q-compare or CompareOverWins.

The present invention is directed to methods of identifying particular structural elements in eukaryotic and prokaryotic nucleic acid, especially RNA molecules, which will interact with other molecules to effect modulation of the RNA. "Modulation" refers to augmenting or diminishing RNA activity or expression. The present invention is outlined in flowchart form in FIG. 1. The structural elements in eukaryotes and prokaryotes are referred to as "molecular interaction sites." These elements contain secondary structure, that is, have three-dimensional form capable of undergoing interaction with "small" molecules and otherwise, and are expected to serve as sites for interacting with "small" molecules, oligomers such as oligonucleotides, and other compounds in therapeutic and other applications.

Figure 1:
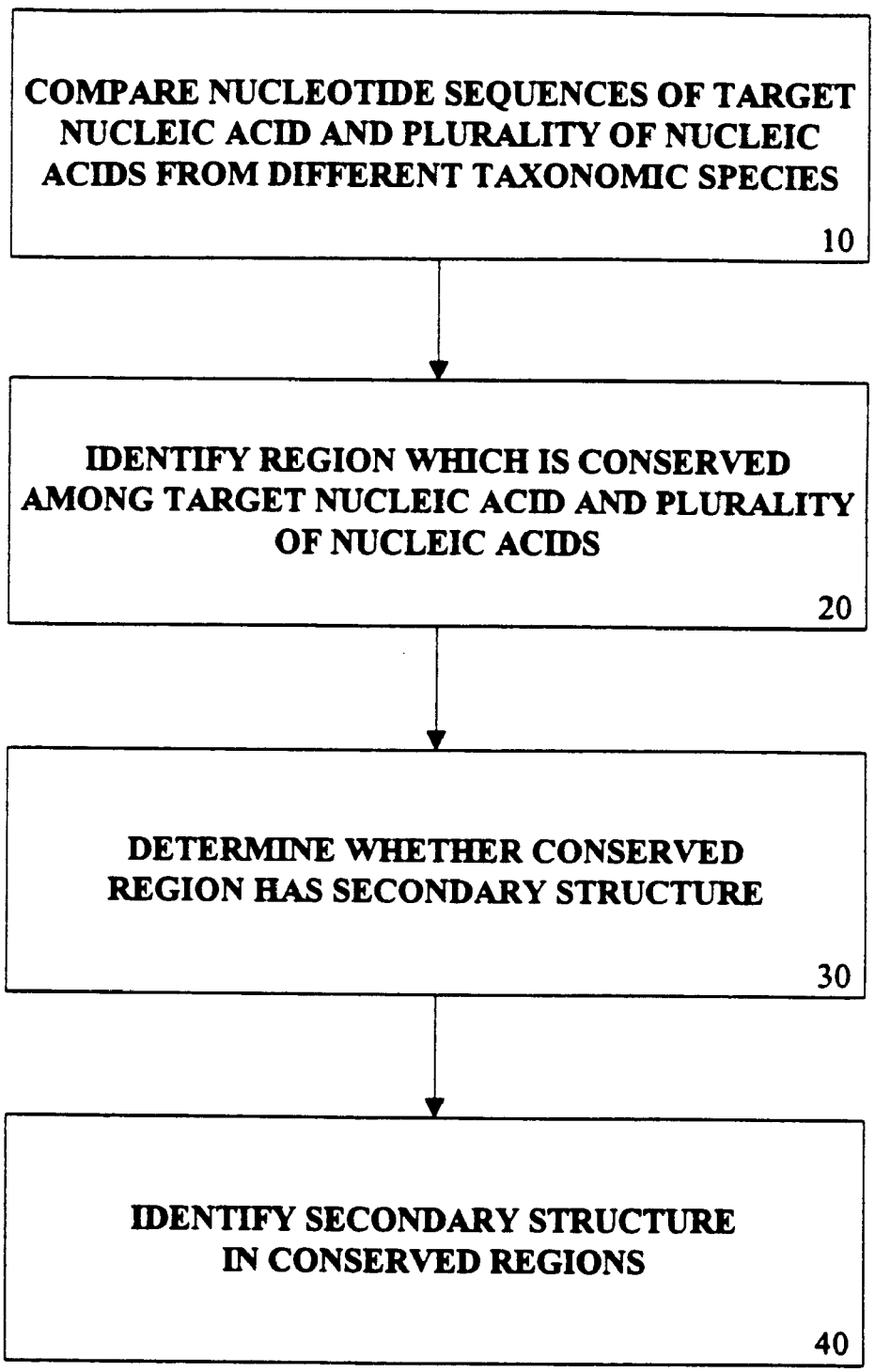
FIG. 1 illustrates a flowchart comprising one preferred set of method steps for identifying molecular interaction sites in eukaryotic and prokaryotic RNA.

Referring to FIG. 1, preferred steps for identifying molecular interaction sites in target nucleic acids are shown in the flow diagram. The nucleotide sequence of the target nucleic acid is compared with the nucleotide sequences of a plurality of nucleic acids from different taxonomic species, 10. The target nucleic acid may be present in eukaryotic cells or prokaryotic cells, the target nucleic acid may be bacterial or viral as well as belonging to a "higher" organism such as human. Any type of nucleic acid can serve as a target nucleic acid. Preferred target nucleic acids include, but are not limited to, messenger RNA (mRNA), pre-messenger RNA (pre-mRNA), transfer RNA (tRNA), ribosomal RNA (rRNA), or small nuclear RNA (snRNA). Initial selection of a particular target nucleic acid can be based upon any functional criteria. Nucleic acids known to be important during inflammation, cardiovascular disease, pain, cancer, arthritis, trauma, obesity, Huntingtons, neurological disorders, or other diseases or disorders, for example, are exemplary target nucleic acids.

Nucleic acids known to be involved in pathogenic genomes such as, for example, bacterial, viral and yeast genomes are exemplary prokaryotic nucleic acid targets. Pathogenic bacteria, viruses and yeast are well known to those skilled in the art. Exemplary nucleic acid targets are shown in Table 1. Applicants' invention, however, is not limited to the targets shown in Table 1 and it is to be understood that the present invention is believed to be quite general.

TABLE 1

Exemplary RNA Targets

| Protein | RNA Target | GenBank # | Therapeutic |
|---|---|---|---|
| 46 kD protein | 3'-UTR stemloop in vimentin mRNA | X56134 | cancer |
| unknown-cGMP | 5'-UTR of | m10058 | cancer |

TABLE 1-continued

Exemplary RNA Targets

| Protein | RNA Target | GenBank # | Therapeutic |
|---|---|---|---|
| regulated | Asialoglycoprotein receptor mRNA | | |
| unknown | unknown | m11025 | unknown |
| unknown insulin regulated protein | 3'-UTR of E-selectin mRNA | unknown | inflammation |
| 30 kD protein | 3'-UTR of lipoprotein lipase mRNA | m15856 | obesity |
| unknown | 5'-UTR of NR2A subunit of NMDA receptor | U09002 | trauma, paid, AD |
| histone binding protein (HBP) | 3'-UTR of histone mRNA + paralogs | x57129 | cancer |
| unknown | 3'-UTR of p53 mRNA | x02469 | cancer |
| p53 | 5'-UTR of mdm2 oncogene mRNA | u39736 | cancer |
| unknown | 5'-UTR of interleukin 1 type receptor (IL-1R1) | m27492 | inflammation |
| none | 5'-UTR of muscle acylphosphatase mRNA | x84195 | musculoskeletal disease |
| ribosomal proteins | 5'-UTR of c-myc in multiple myeloma | V00568 | cancer |
| unknown | 5'-UTR of Huntingtons disease gene | | Huntingtons |
| unknown | 5'-UTR of angiotensin AT | p30556 | cardiovascular disease |
| unknown | zip code sequence in ARC mRNA | d87468 | unknown |
| L-4 | 5'-UTR of L4 ribosomal protein | d23660 | cancer |
| L-32 | 5'-UTR of L32 ribosomal protein | x03342 | cancer |
| unknown | TCTP, translationally controlled tumor protein | x16064 | cancer |
| unknown | 3'-UTR of B-F1-ATPase | d00022 | cancer |
| PU family of proteins, FBF binding factor | 3'-UTR of fem-3 in *C. elegans* | X64962 | unknown |
| unknown | 3'-UTR of myocyte enhancer factor 2 MEF2A | x68505 | metabolic |
| unknown | 5'-UTR of glucose transporter mRNA GLUT1 | k03195 | diabetes |
| 48 kD reticulocyte protein | 3'-UTR of 15-lipoxygenase | M23892 | inflammation |
| La protein | 5'-UTR of ribosomal RNA proteins | | cancer |
| unknown | translational regulation of IL-2 | S82692 | inflammation |
| unknown | 3'-UTR of CaMKIIa mRNA in neurons | u81554 | CNS |
| bicoid (bcd) | BRE 3'-UTR fragment mRNA encoding cad protein | M21069 | under development |
| 48/50 kD protein | 3'-UTR structure protamines 1 | Y00443 | cancer |
| translin (human) TB-RBP (mouse) | protamine 1 mRNA (human testes specific) | Y00443 | cancer |
| translin (human) TB-RBP (mouse) | protamine 2 mRNA | X07862 | unknown |
| translin (human) TB-RBP (mouse) | transition protein mRNA | x14474 | cancer |
| translin (human) TB-RBP (mouse) | Tau mRNA | m13577 | cancer |
| translin (human) TB-RBP (mouse) | myelin basic protein mRNA | x07948 | cancer |
| p75 | 3'-UTR of ribonucleotide reductase R2 | x59618 | cancer |
| 39 kD poly C protein | alpha globin | v00493 | cancer |
| unknown | beta protein | v00497 | metabolic |
| human teratocarcinoma protein p40 | Line-1 mRNA | | cancer, metabolic |
| RPL32 | 5'-UTR hairpin structure in RPL32 family of transcription factor mRNAs with a Y-box sequence | | cancer |
| Y-box proteins | | | cancer |
| telomerase protein | telomerase RNA | AF015950 | cancer |
| ferritin, transferrin | IREs, internal loops in mRNA encoding ferritin and transferrin | | inflammation |
| ribosomal proteins | 5'-UTR of PDGF2/c-sis mRNA | M12873 | inflammation |
| zip code for localization | 3'-UTR of beta actin | | cancer |
| unknown insulin regulated protein | 5'-UTR of ornithine decarboxylase mRNA | x55362 | cancer |
| ribosomal proteins | ornithine decarboxylase antizyme | | cancer |
| unknown | FGF-5 | | inflammation |
| DFR protein factor | 3'-UTR TGE elements in the human oncogene GLI | X07384 | cancer |
| DFR protein factor | 3'-UTR tra-2 of *C. elegans* | | unknown |
| viral capsid protein | 3'-UTR of alfalfa mosaic virus RNA3 | | unknown |
| unknown | BRE Bruno response element in 3'-UTR of drosophila oskar mRNA | | cancer |
| unknown | NRE nanose response element | | cancer |
| unknown | repeated element | | inflammation |
| U1A RDB protein | U1 snRNA | | inflammation |
| CD4O | | X60592 | inflammation |
| IGF-R | | X04434 M24599 | inflammation |
| A1 adenosine receptor | | X68485 | cardiovascular |
| B7-1 | | M27533 | inflammation |
| B7-2 | | | inflammation |
| cyclophilin B | | M60857 M60457 M63573 | inflammation |
| cyclophilin C | | S71018 | transplantation |
| FKBP51 | | | transplantation |
| Th1 cytokines IFN γ | | | inflammation |
| Th1 cytokines IL-12 | | U03187 | inflammation |
| NF-kappa B | | | cancer |
| ICAM-1 | | X06990 | inflammation |
| L-selectin | | X16150 | inflammation |
| VCAM-1 | | M30257 | inflammation |
| Alpha 4 integrin | | X16983 X15356 | inflammation |
| Beta 7 | | U34971 | inflammation |
| MadCAM-1 | | U43628 | inflammation |
| PECAM-1 | | M28526 | inflammation |
| LFA-1 | | Y00796 | inflammation |
| TACE | | | inflammation |
| LFA-3 | | X06296 Y00636 | inflammation |

TABLE 1-continued

Exemplary RNA Targets

| Protein | RNA Target | GenBank # | Therapeutic |
|---|---|---|---|
| CD-18 | | | inflammation |
| ICAM-3 | | X69819 | inflammation |
| ICAM-2 | | X15606 | inflammation |
| CD11a | | M87662 | inflammation |
| protein kinase C-α | | | cancer |
| protein kinase C-β | | X52479 | cancer |
| protein kinase C-δ | | | cancer |
| protein kinase C-ε | | Z22521 | cancer |
| protein kinase C-h | | X65293 | cancer |
| protein kinase C-m | | M55284 | cancer |
| protein kinase C-ζ | | | cancer |
| unknown | | Z15108 | unknown |

Additional nucleic acid targets may be determied inependently or can be selected from publicly available prokaryotic and eukaryotic genetic databases known to those skilled in the art. Preferred databases include, for example, Online Mendelian Inheritance in Man (OMIM), the Cancer Genome Anatomy Project (CGAP), GenBank, EMBL, PIR, SWISS-PROT, and the like. OMIM, which is a database of genetic mutations associated with disease, was developed, in part, for the National Center for Biotechnology Information (NCBI). OMIM can be accessed through the Internet at, for example, http://www.ncbi.nlm.nih.gov/Omim/. CGAP, which is an interdisciplinary program to establish the information and technological tools required to decipher the molecular anatomy of a cancer cell. CGAP can be accessed through the Internet at, for example, http://www.ncbi.nlm.nih.gov/ncicgap/. Some of these databases may contain complete or partial nucleotide sequences. In addition, nucleic acid targets can also be selected from private genetic databases. Alternatively, nucleic acid targets can be selected from available publications or can be determined especially for use in connection with the present invention.

After a nucleic acid target is selected or provided, the nucleotide sequence of the nucleic acid target is determined and then compared to the nucleotide sequences of a plurality of nucleic acids from different taxonomic species. In one embodiment of the invention, the nucleotide sequence of the nucleic acid target is determined by scanning at least one genetic database or is identified in available publications. Preferred databases known and available to those skilled in the art include, for example, the Expressed Gene Anatomy Database (EGAD) and Unigene-Homo Sapiens database (Unigene), GenBank, and the like. EGAD contains a non-redundant set of human transcript (HT) sequences and can be accessed through the Internet at, for example, http://www.tigr.org/tdb/egad/egad.html. Unigene is a system for automatically partitioning GenBank sequences into a non-redundant set of gene-oriented clusters. Each Unigene cluster contains sequences that represent a unique gene, as well as related information such as the tissue types in which the gene has been expressed and map location.

In addition, Unigene contains hundreds of thousands of novel expressed sequence tag (EST) sequences. Unigene can be accessed through the Internet at, for example, http://www.ncbi.nlm.nih.gov/UniGene/. These databases can be used in connection with searching programs such as, for example, Entrez, which is known and available to those skilled in the art, and the like. Entrez can be accessed through the Internet at, for example, http://www.ncbi.nlm.nih.gov/Entrez/. Preferably, the most complete nucleic acid sequence representation available from various databases is used. The GenBank database, which is known and available to those skilled in the art, can also be used to obtain the most complete nucleotide sequence. GenBank is the NIH genetic sequence database and is an annotated collection of all publicly available DNA sequences. GenBank is described in, for example, Nuc. Acids Res., 1998, 26, 1–7, which is incorporated herein by reference in its entirety, and can be accessed by those skilled in the art through the Internet at, for example, http://www.ncbi.nlm.nih.gov/Web/Genbank/index.html. Alternatively, partial nucleotide sequences of nucleic acid targets can be used when a complete nucleotide sequence is not available.

In another embodiment of the present invention, the nucleotide sequence of the nucleic acid target is determined by assembling a plurality of overlapping expressed sequence tags (ESTs). The EST database (dbEST), which is known and available to those skilled in the art, comprises approximately one million different human mRNA sequences comprising from about 500 to 1000 nucleotides, and various numbers of ESTs from a number of different organisms. dbEST can be accessed through the Internet at, for example, http://www.ncbi.nlm.nih.gov/dbEST/index.html. These sequences are derived from a cloning strategy that uses cDNA expression clones for genome sequencing. ESTs have applications in the discovery of new genes, mapping of genomes, and identification of coding regions in genomic sequences. Another important feature of EST sequence information that is becoming rapidly available is tissue-specific gene expression data. This can be extremely useful in targeting selective gene(s) for therapeutic intervention. Since EST sequences are relatively short, they must be assembled in order to provide a complete sequence. Because every available clone is sequenced, it results in a number of overlapping regions being reported in the database.

Figure 2:
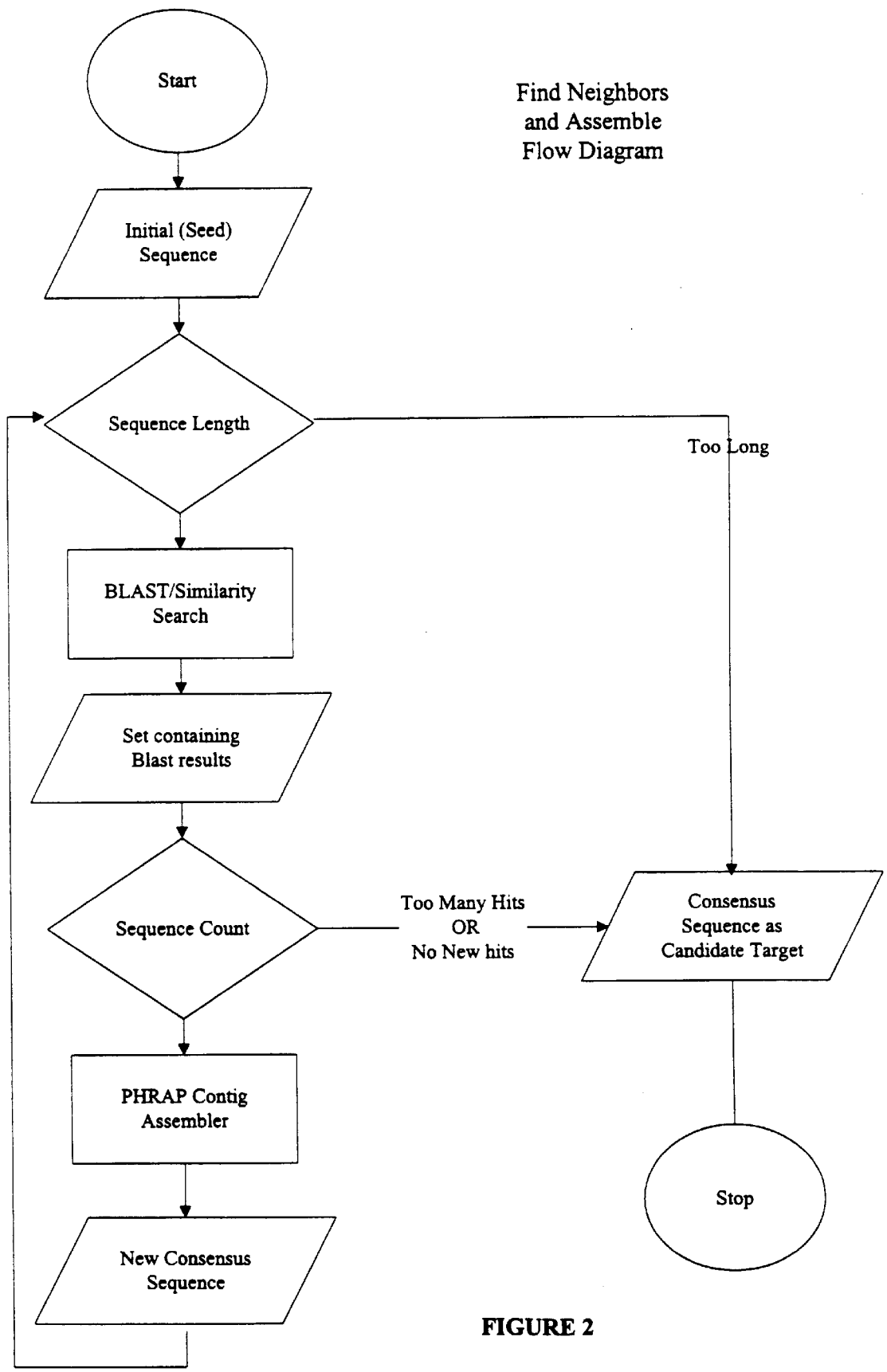
FIG. 2 is a flowchart describing a preferred set of procedures in the Find Neighbors And Assemble ESTBlast protocol.

Assembly of overlapping ESTs extended along both the 5' and 3' directions results in a full-length "virtual transcript." The resultant virtual transcript may represent an already characterized nucleic acid or may be a novel nucleic acid with no known biological function. The Institute for Genomic Research (TIGR) Human Genome Index (HGI) database, which is known and available to those skilled in the art, contains a list of human transcripts. TIGR can be accessed through the Internet at, for example, http://www.tigr.org/. The transcripts were generated in this manner using TIGR-Assembler, an engine to build virtual transcripts and which is known and available to those skilled in the art. TIGR-Assembler is a tool for assembling large sets of overlapping sequence data such as ESTs, BACs, or small genomes, and can be used to assemble eukaryotic or prokaryotic sequences. TIGR-Assembler is described in, for example, Sutton, et al., Genome Science & Tech., 1995, 1, 9–19, which is incorporated herein by reference in its entirety, and can be accessed through the Internet at, for example, ftp://ftp.tigr.org/pub/software/TIGR assembler. In addition, GLAXO-MRC, which is known and available to those skilled in the art, is another protocol for constructing virtual transcripts. In addition, "Find Neighbors and Assemble EST Blast" protocol, which runs on a UNIX platform, has been developed by Applicants to construct virtual transcripts. Preferred steps in the Find Neighbors and Assemble EST Blast protocol is described in the flowchart set forth in FIG. 2. PHRAP is used for sequence assembly within Find Neighbors and Assemble EST Blast. PHRAP can be accessed through the Internet at, for example, http://chimera.biotech.washington.edu/uwgc/tools/phrap.htm. One skilled in the art can construct source code to carry out the preferred steps set forth in FIG. 2.

The nucleotide sequence of the nucleic acid target is compared to the nucleotide sequences of a plurality of nucleic acids from different taxonomic species. A plurality of nucleic acids from different taxonomic species, and the nucleotide sequences thereof, can be found in genetic databases, from available publications, or can be determined especially for use in connection with the present invention. In one embodiment of the invention, the nucleic acid target is compared to the nucleotide sequences of a plurality of nucleic acids from different taxonomic species by performing a sequence similarity search, an ortholog search, or both, such searches being known to perwons of ordinary skill in the art.

The result of a sequence similarity search is a plurality of nucleic acids having at least a portion of their nucleotide sequences which are homologous to at least an 8 to 20 nucleotide region of the target nucleic acid, referred to as the window region. Preferably, the plurality of nucleotide sequences comprise at least one portion which is at least 60% homologous to any window region of the target nucleic acid. More preferably, the homology is at least 70%. More preferably, the homology is at least 80%. Most preferably, the homology is at least 90%. For example, the window size, the portion of the target nucleotide to which the plurality of sequences are compared, can be from about 8 to about 20, preferably 10–15, most preferably about 11–12, contiguous nucleotides. The window size can be adjusted accordingly. A plurality of nucleic acids from different taxonomic species is then preferably compared to each likely window in the target nucleic acid until all portions of the plurality of sequences is compared to the windows of the target nucleic acid. Sequences of the plurality of nucleic acids from different taxonomic species which have portions which are at least 60%, preferably at least 70%, more preferably at least 80%, or most preferably at least 90% homologous to any window sequence of the target nucleic acid are considered as likely homologous sequences.

Sequence similarity searches can be performed manually or by using several available computer programs known to those skilled in the art. Preferably, Blast and Smith-Waterman algorithms, which are available and known to those skilled in the art, and the like can be used. Blast is NCBI's sequence similarity search tool designed to support analysis of nucleotide and protein sequence databases. Blast can be accessed through the Internet at, for example, http://www.ncbi.nlm.nih.gov/BLAST/. The GCG Package provides a local version of Blast that can be used either with public domain databases or with any locally available searchable database. GCG Package v9.0 is a commercially available software package that contains over 100 interrelated software programs that enables analysis of sequences by editing, mapping, comparing and aligning them. Other programs included in the GCG Package include, for example, programs which facilitate RNA secondary structure predictions, nucleic acid fragment assembly, and evolutionary analysis. In addition, the most prominent genetic databases (GenBank, EMBL, PIR, and SWISS-PROT) are distributed along with the GCG Package and are fully accessible with the database searching and manipulation programs. GCG can be accessed through the Internet at, for example, http://www.gcg.com/. Fetch is a tool available in GCG that can get annotated GenBank records based on accession numbers and is similar to Entrez. Another sequence similarity search can be performed with GeneWorld and GeneThesaurus from Pangea. GeneWorld 2.5 is an automated, flexible, high-throughput application for analysis of polynucleotide and protein sequences. GeneWorld allows for automatic analysis and annotations of sequences. Like GCG, GeneWorld incorporates several tools for homology searching, gene finding, multiple sequence alignment, secondary structure prediction, and motif identification. GeneThesaurus 1.0 tm is a sequence and annotation data subscription service providing information from multiple sources, providing a relational data model for public and local data.

Another alternative sequence similarity search can be performed, for example, by BlastParse. BlastParse is a PERL script running on a UNIX platform that automates the strategy described above. BlastParse takes a list of target accession numbers of interest and takes each one through the preferred processes described in the flowchart set forth in FIG. 3. BlastParse parses all the GenBank fields into "tab-delimited" text that can then be saved in a "relational database" format for easier search and analysis, which provides flexibility. The end result is a series of completely parsed GenBank records that can be easily sorted, filtered, and queried against, as well as an annotations-relational database.

Figure 3:
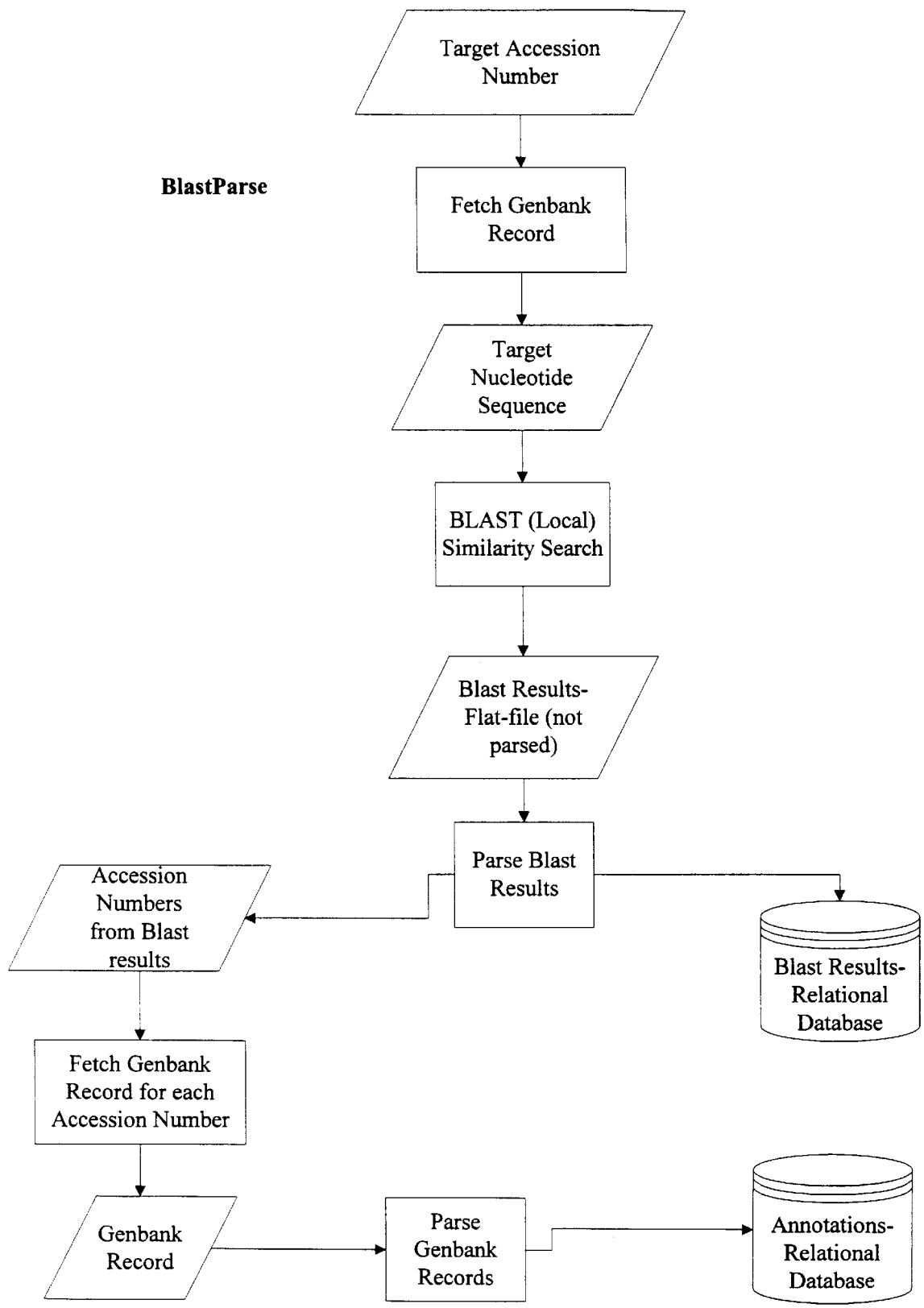
FIG. 3 is a flowchart describing preferred steps in the BlastParse protocol.

Preferably, the plurality of nucleic acids from different taxonomic species which have homology to the target nucleic acid, as described above in the sequence similarity search, are further delineated so as to find orthologs of the target nucleic acid therein. An ortholog is a term defined in gene classification to refer to two genes in widely divergent organisms that have sequence similarity, and perform similar functions within the context of the organism. In contrast, paralogs are genes within a species that occur due to gene duplication, but have evolved new functions, and are also referred to as isotypes. Optionally, paralog searches can also be performed. By performing an ortholog search, an exhaustive list of homologous sequences from as diverse organisms as possible is obtained. Subsequently, these sequences are analyzed to select the best representative sequence that fits the criteria for being an ortholog. An ortholog search can be performed by programs available to those skilled in the art including, for example, Compare. Preferably, an ortholog search is performed with access to complete and parsed GenBank annotations for each of the sequences. Currently, the records obtained from GenBank are "flat-files", and are not ideally suited for automated analysis. Preferably, the ortholog search is performed using a Q-Compare program. Preferred steps of the Q-Compare protocol are described in the flowchart set forth in FIG. 4. The Blast Results-Relation database, depicted in FIG. 3, and the Annotations-Relational database, depicted in FIG. 3, are used in the Q-Compare protocol, which results in a list of ortholog sequences to compare in the interspecies sequence comparisons programs described below.

The above-described similarity searches provide results based on cut-off values, referred to as e-scores. E-scores represent the probability of a random sequence match within a given window of nucleotides. The lower the e-score, the better the match. One skilled in the art is familiar with e-scores. The user defines the e-value cut-off depending upon the stringency, or degree of homology desired, as described above. In embodiments of the invention where prokaryotic molecular interaction sites are identified, it is preferred that any homologous nucleotide sequences that are identified be non-human.

In another embodiment of the present invention, the nucleotide sequences of a plurality of nucleic acids from different taxonomic species are compared to the nucleotide sequence of the target nucleic acid by performing a sequence similarity search using dbEST, or the like, and constructing virtual transcripts. Using EST information is useful for two distinct reasons. First, the ability to identify orthologs for human genes in evolutionarily distinct organisms in GenBank database is limited. As more effort is directed towards identifying ESTs from these evolutionarily distinct organisms, dbEST is likely to be a better source of ortholog information.

Second, the attempt to sequence human genome is less than 10% complete. Thus, it is likely that the human dbEST will provide more information for identifying primary targets as the sequence of the human genome nears completion. EST sequences are short and need to be assembled to be used. Preferably, a sequence similarity search is performed using Smith-Waterman algorithms, as described above, under high stringency against dbEST excluding human sequences. Because dbEST contains sequencing errors, including insertions and deletions, in order to accurately search for new sequences, the search method used should allow for these gaps. Because every available clone is sequenced, it results in a number of overlapping regions being reported in the database. A full-length or partial "virtual transcript" for non-human RNAs is constructed by a process whereby overlapping EST sequences are extended along both the 5' and 3' directions, until a "full-length" transcript is obtained. In another embodiment of the invention, a chimeric virtual transcript is constructed.

The resultant virtual transcript may represent an already characterized RNA molecule or could be a novel RNA molecule with no known biological function. As described above, TIGR HGI database makes available an engine to build virtual transcripts called TIGR-Assembler. GLAXO-MRC and GeneWorld from Pangea provide for construction of virtual transcripts as well. As described above, Find Neighbors and Assemble EST Blast can also be used to build virtual transcripts.

Referring to FIG. 1, after the orthologs or virtual transcripts described above are obtained through either the sequence similarity search or the ortholog search, at least one sequence region which is conserved among the plurality of nucleic acids from different taxonomic species and the target nucleic acid is identified, 20. Interspecies sequence comparisons can be performed using numerous computer programs which are available and known to those skilled in the art. Preferably, interspecies sequence comparison is performed using Compare, which is available and known to those skilled in the art. Compare is a GCG tool that allows pair-wise comparisons of sequences using a window/stringency criterion. Compare produces an output file containing points where matches of specified quality are found. These can be plotted with another GCG tool, DotPlot.

Figure 4:
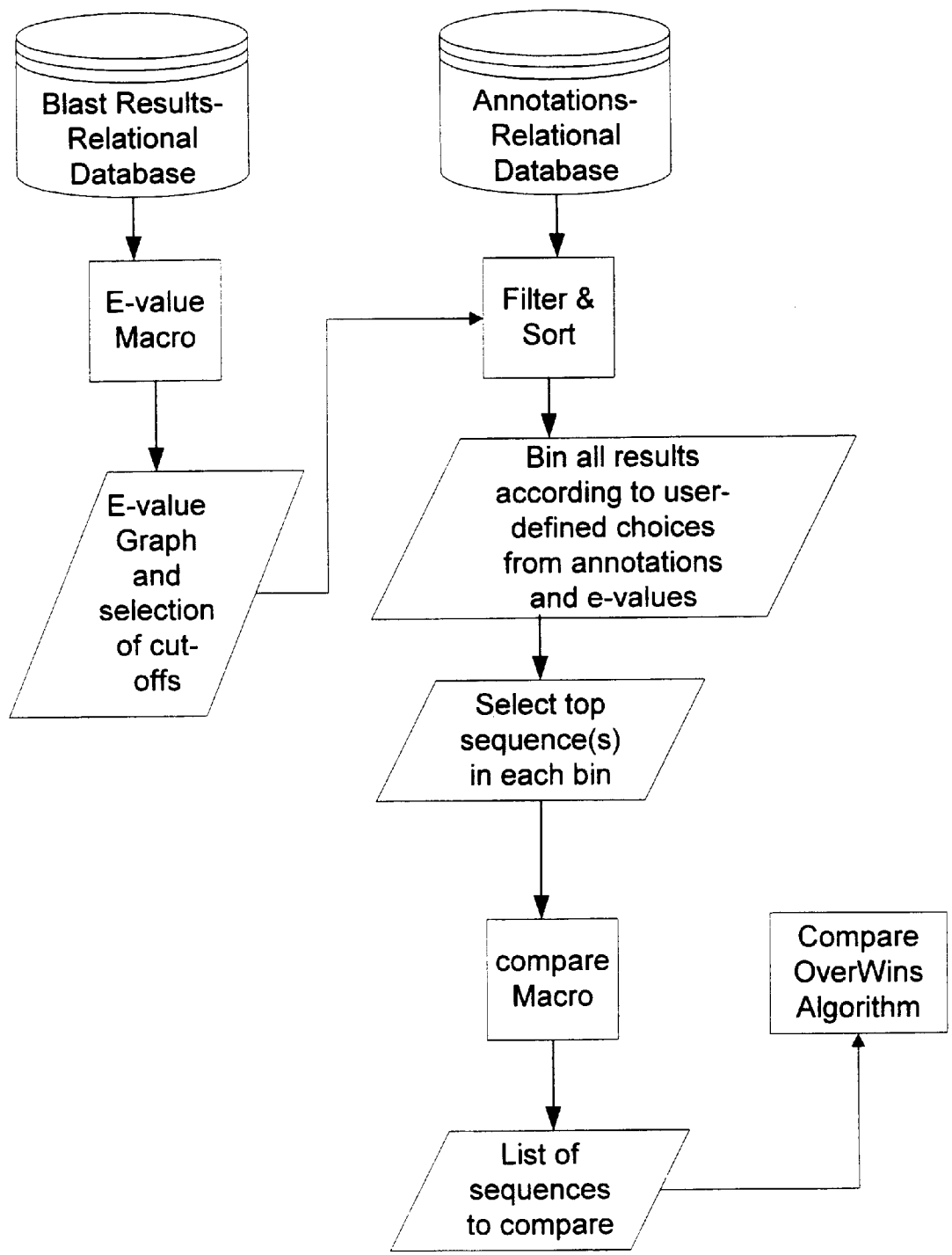
FIG. 4 is a flowchart describing preferred steps in the Q-Compare protocol.
Figure 5A:
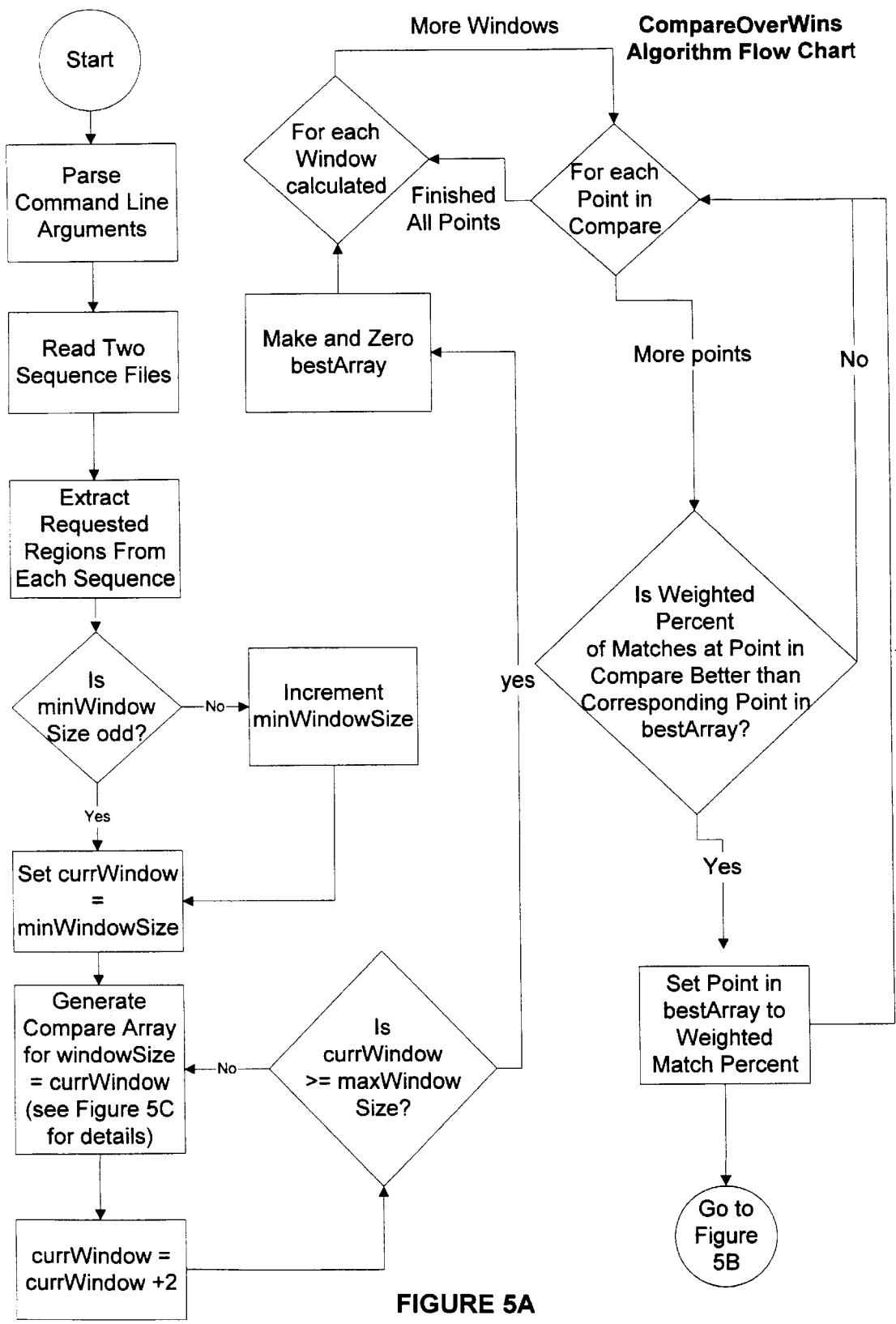
FIGS. 5A, 5B, and 5C illustrate flowcharts describing preferred steps in the CompareOverWins protocol.
Figure 5B:
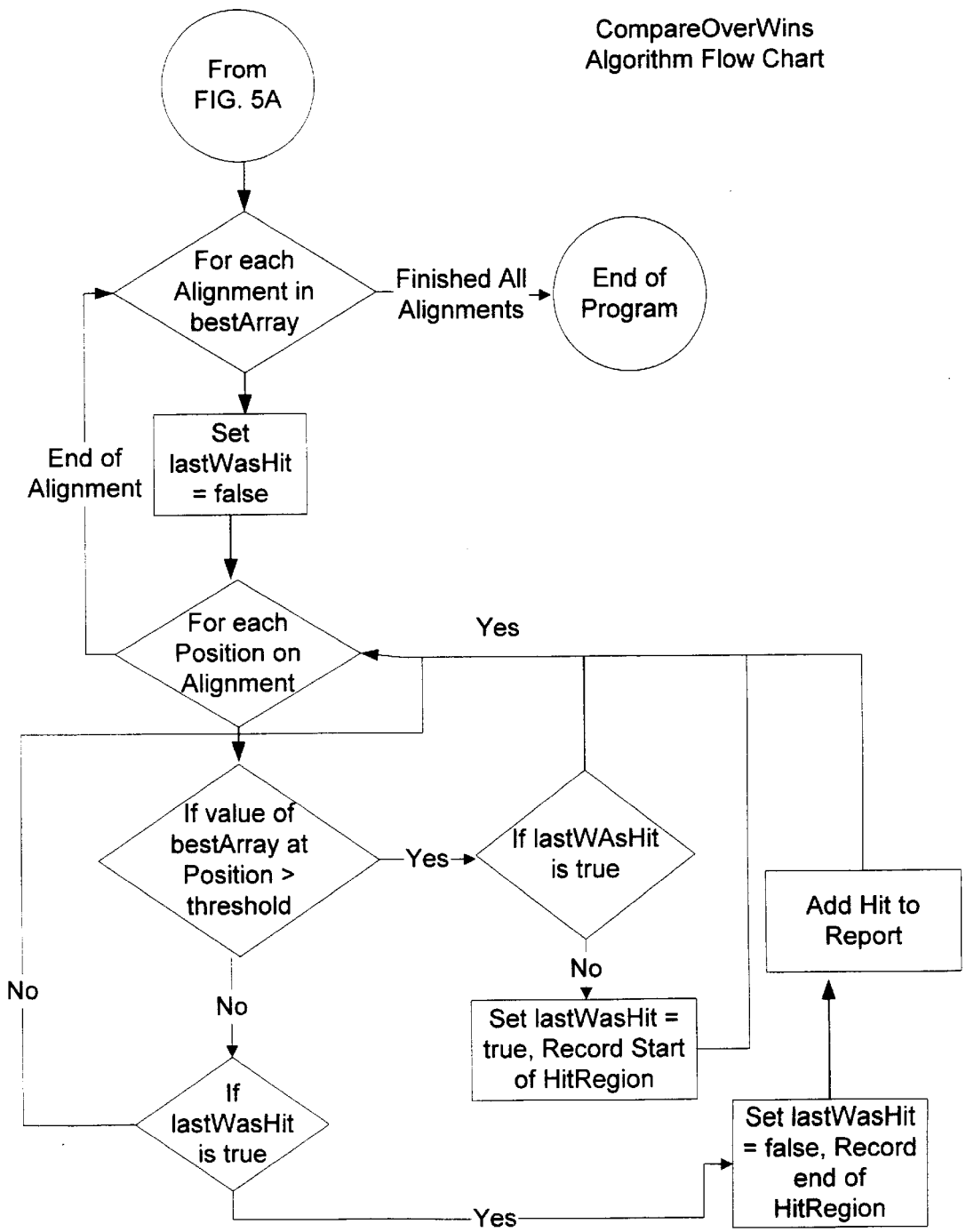
Figure 5C:
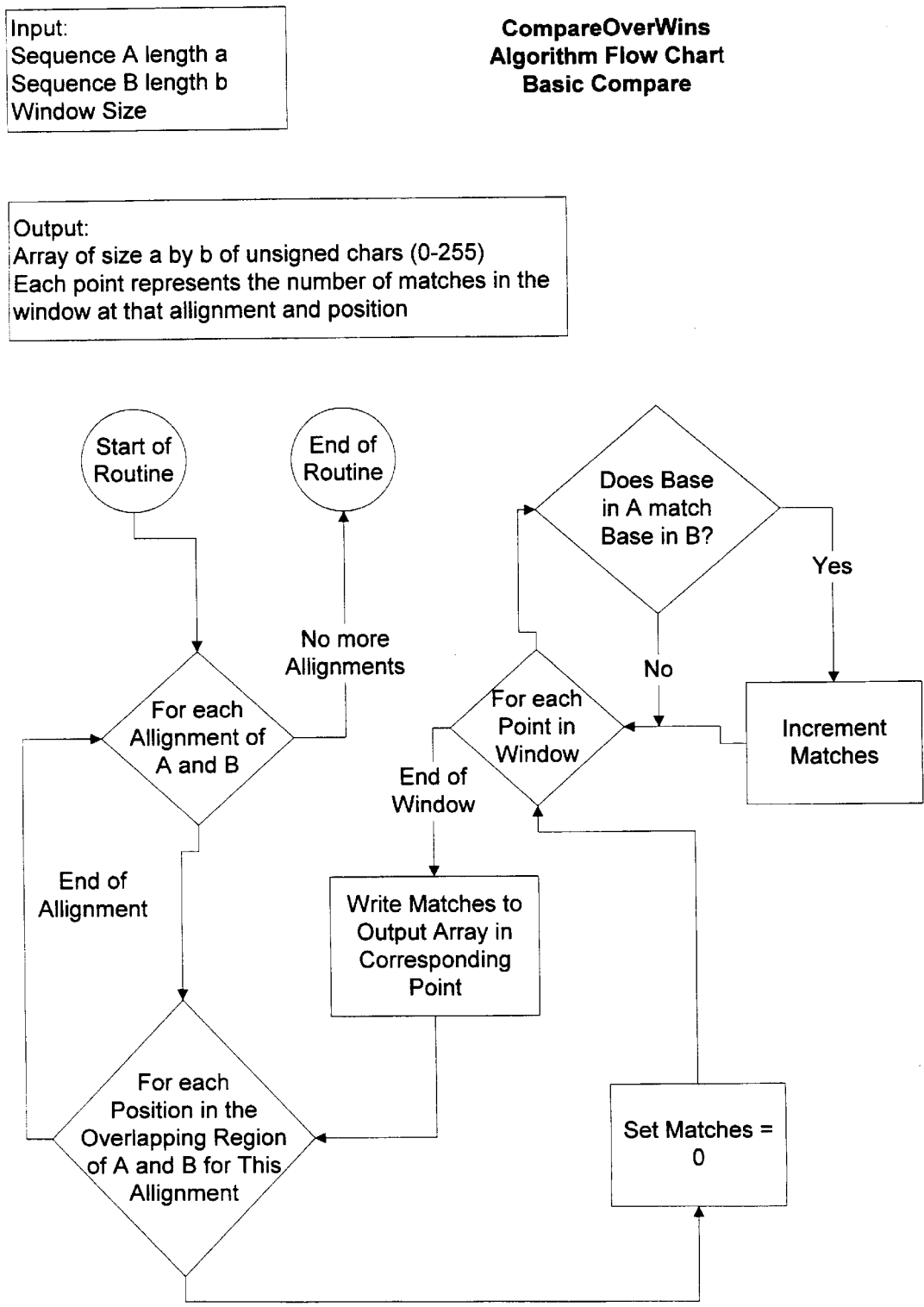

Alternatively, the identification of a conserved sequence region is performed by interspecies sequence comparisons using the ortholog sequences generated from Q-Compare in combination with CompareOverWins, as described above. Preferably, the list of sequences to compare, i.e., the ortholog sequences, generated from Q-Compare, as described in FIG. 4, is entered into the CompareOverWins algorithm. Preferred steps in the CompareOverWins are described in FIGS. 5A, 5B, and 5C. Preferably, interspecies sequence comparisons are performed by a pair-wise sequence comparison in which a query sequence is slid over a window on the master target sequence. Preferably, the window is from about 10 to about 30 contiguous nucleotides. More preferably, the window is 21 nucleotides. If the number of identical bases (matches) within this window reaches a user-defined threshold, a score is given.

Figure 6:
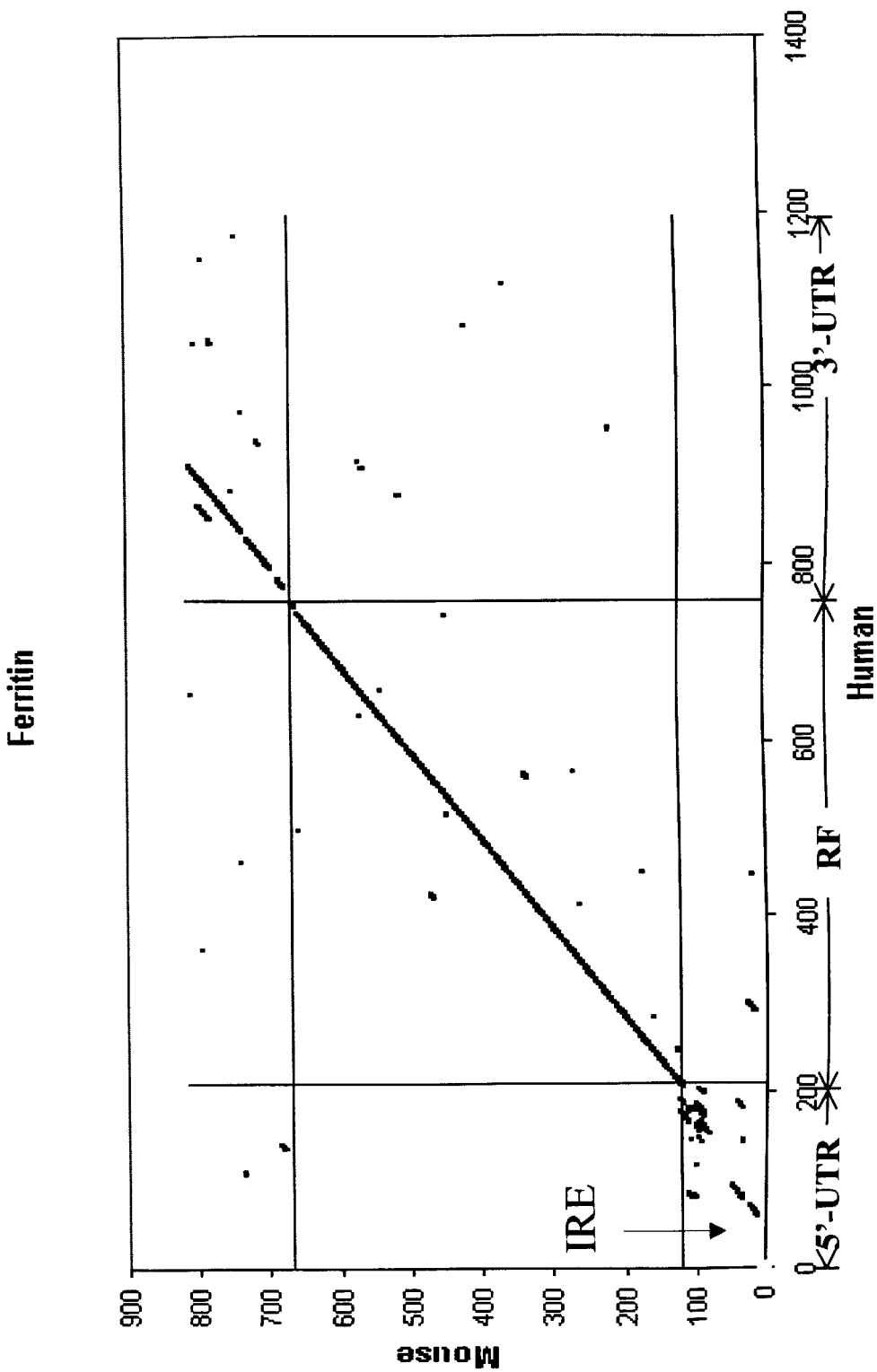
FIG. 6 is representative scatter plot of an interspecies sequence comparison between mouse and human for a ferritin RNA.

Sequence homology between the window sequence of the target nucleic acid and the query sequence of any of the plurality of nucleic acid sequences obtained as described above, is preferably at least 60%, more preferably at least 70%, more preferably at least 80%, and most preferably at least 90%. This process is repeated until every base on the query nucleic acid, which is a member of the plurality of nucleic acids described above, has been compared to every base on the master target sequence. The resulting scoring matrix can be plotted as a scatter plot. Based on the match density at a given location, there may be no dots, isolated dots, or a set of dots so close together that they appear as a line. The presence of lines, however small, indicates primary sequence homology. A representative scatter plot of such interspecies sequence comparison is depicted in FIG. 6. Sequence conservation within nucleic acid molecules, particularly the UTRs of RNA, in divergent species is likely to be an indicator of conserved regulatory elements that are also likely to have a secondary structure. The results of the interspecies sequence comparison can be analyzed using MS Excel and visual basic tools in an entirely automated manner as known to those skilled in the art.

Referring to FIG. 1, after at least one region that is conserved between the nucleotide sequence of the nucleic acid target and the plurality of nucleic acids from different taxonomic species, preferably via the orthologs, is identified, the conserved region is analyzed to determine whether it contains secondary structure, 30. Determining whether the identified conserved regions contain secondary structure can be performed by a number of procedures known to those skilled in the art. Determination of secondary structure is preferably performed by self complementarity comparison, alignment and covariance analysis, secondary structure prediction, or a combination thereof.

In one embodiment of the invention, secondary structure analysis is performed by alignment and covariance analysis. Numerous protocols for alignment and covariance analysis are known to those skilled in the art. Preferably, alignment is performed by ClustalW, which is available and known to those skilled in the art. ClustalW is a tool for multiple sequence alignment that, although not a part of GCG, can be added as an extension of the existing GCG tool set and used with local sequences. ClustalW can be accessed through the Internet at, for example, http://dot.imgen.bcm.tmc.edu:9331/multi-align/Options/clustalw.html. ClustalW is also described in Thompson, et al., *Nuc. Acids Res.*, 1994, 22, 4673–4680, which is incorporated herein by reference in its entirety. These processes can be scripted to automatically use conserved UTR regions identified in earlier steps. Seqed, a UNIX command line interface available and known to those skilled in the art, allows extraction of selected local regions from a larger sequence. Multiple sequences from many different species can be clustered and aligned for further analysis.

Covariation is a process of using phylogenetic analysis of primary sequence information for consensus secondary structure prediction. Covariation is described in the following references, each of which is incorporated herein by reference in their entirety: Gutell, et al, "Comparative Sequence Analysis Of Experiments Performed During Evolution" In Ribosomal RNA Group I Introns, Green, Ed., Austin:Landes, 1996; Gautheret, et al., *Nuc. Acids Res.*, 1997, 25, 1559–1564; Gautheret, et al., *RNA*, 1995, 1, 807–814; Lodmell, et al., *Proc. Natl Acad Sci. USA,* 1995, 92, 10555–10559; Gautheret, et al, *J Mol. Biol.,* 1995,248, 27–43; Gutell, *Nuc. Acids Res.,* 1994, 22, 3502–3517; Gutell, *Nuc. Acids Res.,* 1993, 21, 3055–3074; Gutell, *Nuc. Acids Res.,* 1993, 21, 3051–3054; Woese, *Proc. Natl. Acad. Sci. USA,* 1989, 86, 3119–3122; and Woese, et al., *Nuc. Acids Res.,* 1980, 8, 2275–2293. Preferably, covariance software is used for covariance analysis. Preferably, Covariation, a set of programs for the comparative analysis of RNA structure from sequence alignments, is used. Covariation uses phylogenetic analysis of primary sequence information for consensus secondary structure prediction. Covariation can be obtained through the Internet at, for example, http://www.mbio.ncsu.edu/RNaseP/info/programs/programs.html. A complete description of a version of the program has been published (Brown, J. W. 1991 Phylogenetic analysis of RNA structure on the Macintosh computer. CABIOS7:391–393). The current version is v4.1, which can perform various types of covariation analysis from RNA sequence alignments, including standard covariation analysis, the identification of compensatory base-changes, and mutual information analysis. The program is well-documented and comes with extensive example files. Compiled as a stand-alone program; it does not require Hypercard (although a much smaller 'stack' version is included). This program will run in any Macintosh environment running MacOS v7.1 or higher. Faster processor machines (68040 or PowerPC) is suggested for mutual information analysis or the analysis of large sequence alignments.

In another embodiment of the invention, secondary structure analysis is performed by secondary structure prediction. There are a number of algorithms that predict RNA secondary structures based on thermodynamic parameters and energy calculations. Preferably, secondary structure prediction is performed using either M-fold or RNA Structure 2.52. M-fold can be accessed through the Internet at, for example, http://www.ibc.wustl.edu/zuker/ma/form2.cgi or can be downloaded for local use on UNIX platforms. M-fold is also available as a part of GCG package. RNA Structure 2.52 is a windows adaptation of the M-fold algorithm and can be accessed through the Internet at, for example, http://128.151.176.70/RNAstructure.html.

Figure 7:
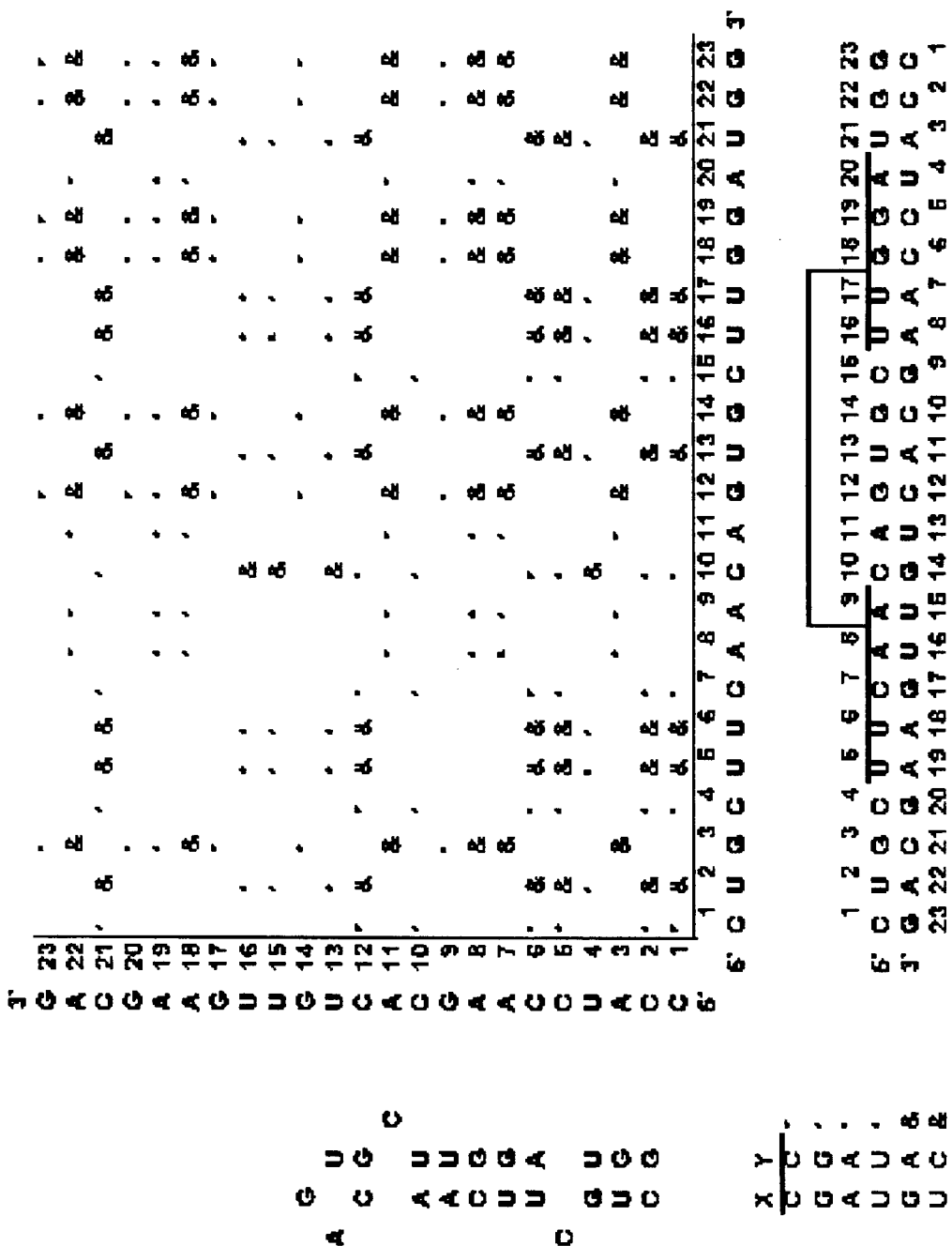
FIG. 7 shows an example of self complementation analysis of a single sequence.
Figure 8:
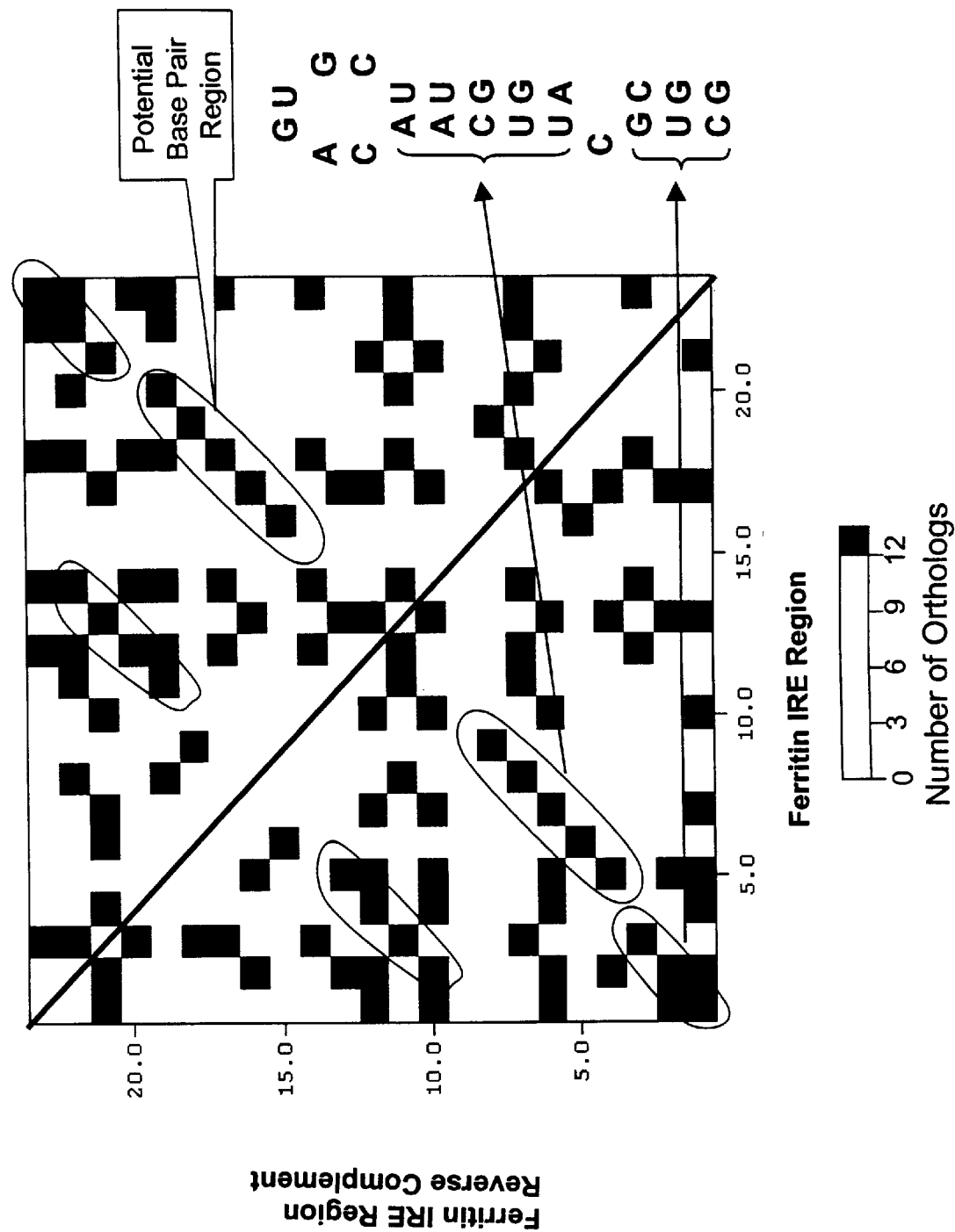
FIG. 8 shows an overlay of self-complementarity plots of certain orthologs, and selection for the most repetitive pattern in each, resulting in a minimal number of possible folded configurations as depicted in the diagonal strings of blocks.

In another embodiment of the invention, secondary structure analysis is performed by self complementarity comparison. Preferably, self complementarity comparison is performed using Compare, described above. More preferably, Compare can be modified to expand the pairing matrix to account for G-U or U-G basepairs in addition to the conventional Watson-Crick G-C/C-G or A-U/U-A pairs. Such a modified Compare program (modified Compare) begins by predicting all possible base-pairings within a given sequence. As described above, a small but conserved region, preferably a UTR, is identified based on primary sequence comparison of a series of orthologs. In modified Compare, each of these sequences is compared to its own reverse complement. FIG. 7 depicts an exemplary self complementarity analysis. Allowable base-pairings include Watson-Crick A-U, G-C pairing and non-canonical G-U pairing. An overlay of such self complementarity plots of all available orthologs, and selection for the most repetitive pattern in each, results in a minimal number of possible folded configurations. FIG. 8 shows an exemplary overlay. These overlays can then used in conjunction with additional constraints, including those imposed by energy considerations described above, to deduce the most likely secondary structure.

A result of the secondary structure analysis described above, whether performed by alignment and covariance, self complementarity analysis, secondary structure predictions, such as using M-fold or otherwise, is the identification of secondary structure in the conserved regions among the target nucleic acid and the plurality of nucleic acids from different taxonomic species, 40. Exemplary secondary structures that may be identified include, but are not limited to, bulges, loops, stems, hairpins, knots, triple interacts, cloverleafs, or helices, or a combination thereof. Alternatively, new secondary structures may be identified.

In another embodiment of the invention, once the secondary structure of the conserved region has been identified, as described above, at least one structural motif for the conserved region having secondary structure is identified. These structural motifs correspond to the identified secondary structures described above. For example, analysis of secondary structure by self complementation may provide one type of secondary structure, whereas analysis by M-fold may provide another secondary structure. All the possible secondary structures identified by secondary structure analysis described above are, thus, represented by a family of structural motifs.

Once the secondary structure(s) of the target nucleic acids, as well as the secondary structures of nucleic acids from different taxonomic species, have been identified, further nucleic acids can be identified by searching on the basis of structure, rather than by primary nucleotide sequence, as described above. Additional nucleic acids which have secondary structure similar or identical to the secondary structure found as described above can be identified by constructing a family of descriptor elements for the structural motifs described above, and identifying other nucleic acids having secondary structures corresponding to the descriptor elements. The combination of any or all of the nucleic acids having secondary structure can be compiled into a database. The entire process can be repeated with a different target nucleic acid to generate a plurality of different secondary structure groups which can be compiled into the database. Thus, databases of molecular interaction sites can be compiled by performing by the invention described herein.

Figure 9:
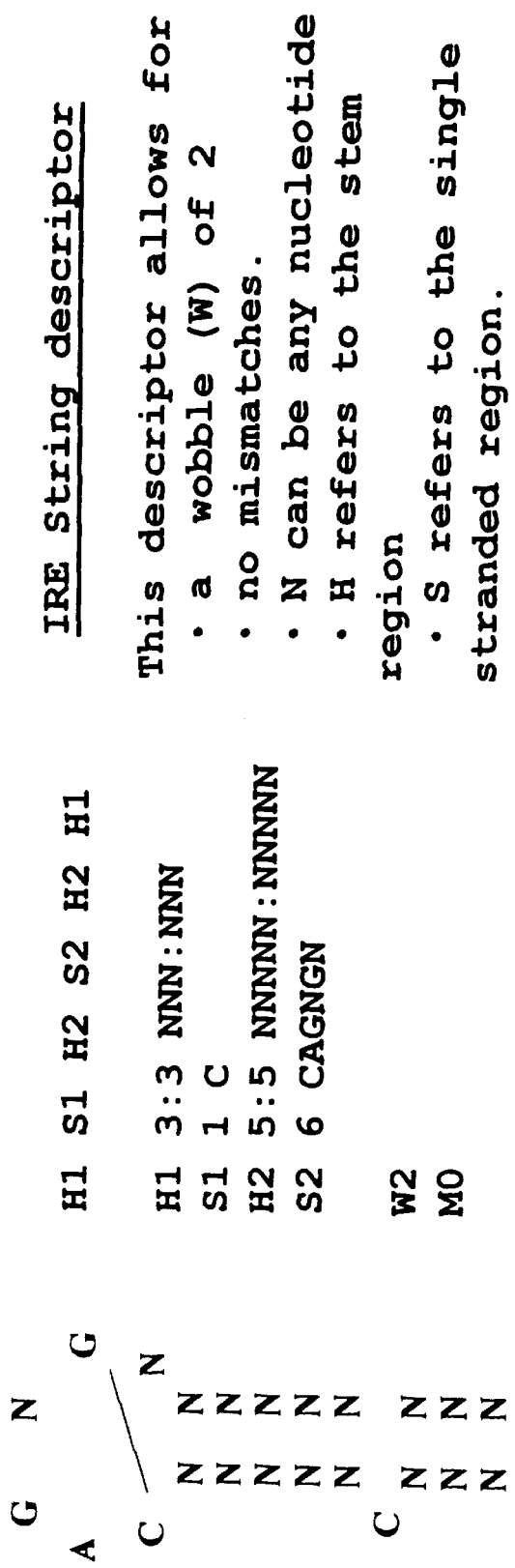
FIG. 9 shows an exemplary descriptor.

After the hypothetical structure motifs are determined from the secondary structure analysis described above, a family of structure descriptor elements is constructed. Preferably, the structural motifs described above are converted into a family of descriptor elements. An exemplary descriptor element is shown in FIG. 9. One skilled in the art is familiar with construction of descriptors. Structure descriptors are described in, for example, Laferriere, et al, *Comput. Appl. Biosci.,* 1994, 10, 211–212, incorporated herein by reference in its entirety. A different structure descriptor element is constructed for each of the structural motifs identified from the secondary structure analysis. Briefly, the secondary structure is converted to a generic text string, such as shown in FIG. 9. For novel motifs, further biochemical analysis such as chemical mapping or mutagenesis may be needed to confirm structure predictions. Descriptor elements may be defined to have various stringency.

For example, referring to FIG. 9, the region termed H1, which comprises the first region of the stem, can be described as NNN:NNN, which contemplates any complementary base pairing including G-C, C-G, A-U, and U-A. The H1 region may also be designated so as to include only C-G or A-U, etc., base pairing. In addition, the descriptor elements can be defined to allow for a wobble. Thus, descriptor elements can be defined to have any level of stringency desired by the user. Applicants' invention, thus, is also directed to a database comprising different descriptor elements.

After a family of structure descriptor elements is constructed, nucleic acids having secondary structure which correspond to the structure descriptor elements are identified. Preferably, nucleic acids having secondary structure which correspond to the structure descriptor elements are identified by searching at least one database, performing clustering and analysis, identifying orthologs, or a combination thereof. Thus, the identified nucleic acids have secondary structure which falls within the scope of the secondary structure defined by the descriptor elements. Thus, the identified nucleic acids have secondary structure identical to nearly identical, depending on the stringency of the descriptor elements, to the target nucleic acid.

In one embodiment of the invention, nucleic acids having secondary structure which correspond to the structure descriptor elements are identified by searching at least one database. Any genetic database can be searched. Preferably, the database is a UTR database, which is a compilation of the untranslated regions in messenger RNAs. A UTR database is accessible through the Internet at, for example, ftp://area.ba.cnr.it/pub/embnet/database/utr/. Preferably the database is searched using a computer program, such as, for example, Rnamot, a UNIX-based motif searching tool available from Daniel Gautheret. Each "new" sequence that has the same motif is then queried against public domain databases to identify additional sequences. Results are analyzed for recurrence of pattern in UTRs of these additional ortholog sequences, as described below, and a database of RNA secondary structures is built. One skilled in the art is familiar with Rnamot. Briefly, Rnamot takes a descriptor string, such as the one shown in FIG. 9, and searches any Fasta format database for possible matches. Descriptors can be very specific, to match exact nucleotide(s), or can have built-in degeneracy. Lengths of the stem and loop can also be specified. Single stranded loop regions can have a variable length. G-U pairings are allowed and can be specified as a wobble parameter. Allowable mismatches can also be included in the descriptor definition. Functional significance is assigned to the motifs if their biological role is known based on previous analysis. Known regulatory regions such as Iron Response Element have been found using this technique (see, Example 1 below). In embodiments of the invention in which a database containing prokaryotic molecular interaction sites is compiled, it is preferable to refrain from searching human sequences or, alternatively, discarding human sequences when found.

In another embodiment of the invention, the nucleic acids identified by searching databases such as, for example, searching a UTR database using Rnamot, are clustered and analyzed so as to determine their location within the genome. The results provided by Rnamot simply identify sequences containing the secondary structure but do not give any indication as to the location of the sequence in the genome. Clustering and analysis is preferably performed with ClustalW, as described above.

In another embodiment of the invention, after clustering and analysis is performed as described above, orthologs are identified as described above. However, in contrast to the orthologs identified above, which were solely identified on the basis of their primary nucleotide sequences, these new orthologous sequences are identified on the basis of structure using the nucleic acids identified using Rnamot. Identification of orthologs is preferably performed by BlastParse or Q-Compare, as described above. In embodiments of the invention in which a database containing prokaryotic molecular interaction sites is compiled, it is preferable to refrain from finding human orthologs or, alternatively, discarding human orthologs when found.

After nucleic acids having secondary structures which correspond to the structure descriptor elements are identified, any or all of the nucleotide sequences can be compiled into a database by standard compiling protocols known to those skilled in the art. One database may contain eukaryotic molecule interaction sites and another database may contain prokaryotic molecule interaction sites The present invention is also directed to oligonucleotides comprising a molecular interaction site that is present in the RNA of a selected organism and in the RNA of at least one preferably several additional organisms. The nucleotide sequence of the oligonucleotide is selected to provide the secondary structure of the molecular interaction sites described above. The nucleotide sequence of the oligonucleotide is preferably the nucleotide sequence of the target nucleic acids described above. Alternatively, the nucleotide sequence is preferably the nucleotide sequence of nucleic acid from a plurality of different taxonomic species which also contain the molecular interaction site. The molecular interaction site serves as a binding site for at least one molecule which, when bound to the molecular interaction site, modulates the expression of the RNA in the selected organism.

The present invention is also directed to oligonucleotides comprising a molecular interaction site that is present in a prokaryotic RNA and in at least one additional prokaryotic RNA, wherein the molecular interaction site serves as a binding site for at least one molecule which, when bound to the molecular interaction site, modulates the expression of the prokaryotic RNA. The additional organism is selected from all all eukaryotic and prokaryotic organisms and cells but is not the same organism as the selected organism. Oligonucleotides, and modifications thereof, are well known to those skilled in the art. The oligonucleotides of the invention can be used, for example, as research reagents to detect, for example, naturally occurring molecules which bind the molecular interaction sites. The oligonucleotides of the invention can also be used as decoys to compete with naturally-occurring molecular interaction sites within a cell for research, diagnostic and therapeutic applications. Molecules which bind to the molecular interaction site modulate, either by augmenting or diminishing, the expression of the RNA. The oligonucleotides can also be used in agricultural, industrial and other applications.

The present invention is also directed to pharmaceutical compositions comprising the oligonucleotides described above in combination with a pharmaceutical carrier. A "pharmaceutical carrier" is a pharmaceutically acceptable solvent, diluent, suspending agent or any other pharmacologically inert vehicle for delivering one or more nucleic acids to an animal, and are well known to those skilled in the art. The carrier may be liquid or solid and is selected, with the planned manner of administration in mind, so as to provide for the desired bulk, consistency, etc., when combined with the other components of a pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The following examples are meant to be exemplary of the preferred embodiments of the invention and are not meant to be limiting.

EXAMPLES

Example 1

The Iron Responsive Element

1. Selecting RNA Target

To illustrate the strategy for identifying small molecule interaction sites, the iron responsive element (IRE) in the mRNA encoded by the human ferritin gene is identified. The IRE is a typical example of an RNA structural element that is used to control the level of translation of mRNAs associated with iron metabolism. The structure of the IRE was recently determined using NMR spectroscopy (#10372, #10504). In addition, NMR analysis of IRE structure is described in Gdaniec, et al., *Biochem.*, 1998, 37, 1505–1512 and Addess, et al., *J. Mol. Biol*, 1997, 274, 72–83. The IRE is an RNA element of approximately 30 nucleotides that folds into a hairpin structure and binds a specific protein. Because this structure has been so well studied and it known to appear in the mRNA of many speicies, it serves an an excellent example of how Applicants' methodology works.

2. Determining Nucleotide Sequence of the RNA Target

The human mRNA sequence for ferritin is used as the initial mRNA of interest or master sequence. The ferritin protein sequence is also used in the anayisis, particularly in the initial steps used to find related sequences. In the case of human ferritin gene, the best input is the full length annotated mRNA and protein sequence obtained from UNI-GENE. However, for many genes of interest the same level of detailed information is not available. In these cases, alternative sources of master sequence information is obtained from sources such as, for example, GenBank, TIGR, dbEST division of GenBank or from sequence information obtained from private laboratories. Applicants' methods work using any level of input sequence information, but requires fewer steps with a high quality annotated input sequence.

3. Identifying Similar Sequences

Figure 10:
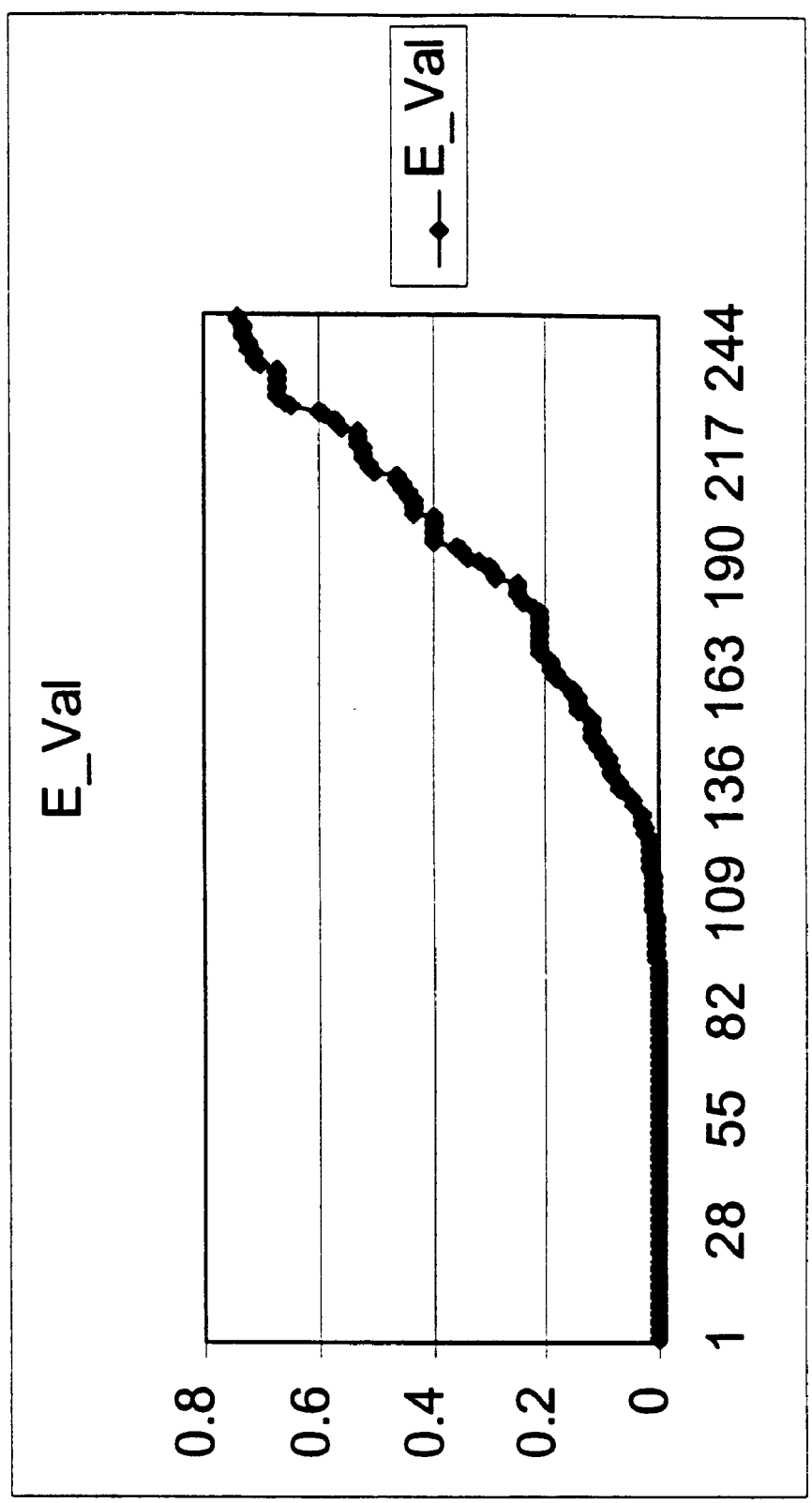
FIG. 10 shows a set of e-value scores for ferritin.

An early step in the process is to use the master sequence (nucleotide or protein) to find and rank related sequences in the database (orthologs and paralogs). Sequence similarity search algorithms are used for this purpose. All sequence similarity algorithms calculate a quantitative measure of similarity for each result compared with the master sequence. An expample of a quantitative result is an E-value obtained from the Blast algorithm. The E-values for a blast search of the non-redundant GenBank database using ferritin mRNA as the query sesquence illustrates the use of quantitative analysis of sequence similarity searches. The E-value is the probability that a match between a query sequence and a database sequence occurs due to random chance. Therefore, the lower an E-value the more likely that two sequences are truly related. A plot of the lowest E-value scores for ferritin is shown in FIG. 10. Sequences that meet the cutoff criteria are selected for more detailed comparisons according to a set of rules described below. Since the objetive of the sequence similarity search to find distantly related orthologs and paralogs it is essential that the cutoff criteria not be too stringent, or the target of the search will be excluded.

4. Identification of Conserved Regions

Identification of conserved regions is performed by pairwise sequence comparisons using Q-Compare in conjunction with CompareOverWins. Conservation of structure between genes with related function from different species is a major indication that can be used to find good drug binding sites. Conserved structure can be identified by using distantly related sequences and piecing together the remnants of conseved sequence combining it with an analysis of potential structure. Sequence comparisons are made between pairs of mRNAs from different species using Q-compare that can identify traces of sequence conservation from even very divergent organisms. Q-compare, in conjuction with CompareOverWins, compares every region of each sequence by sliding one sequence over the other from end to end and measuring the number of matches in a window of a specific size.

Figure 11:
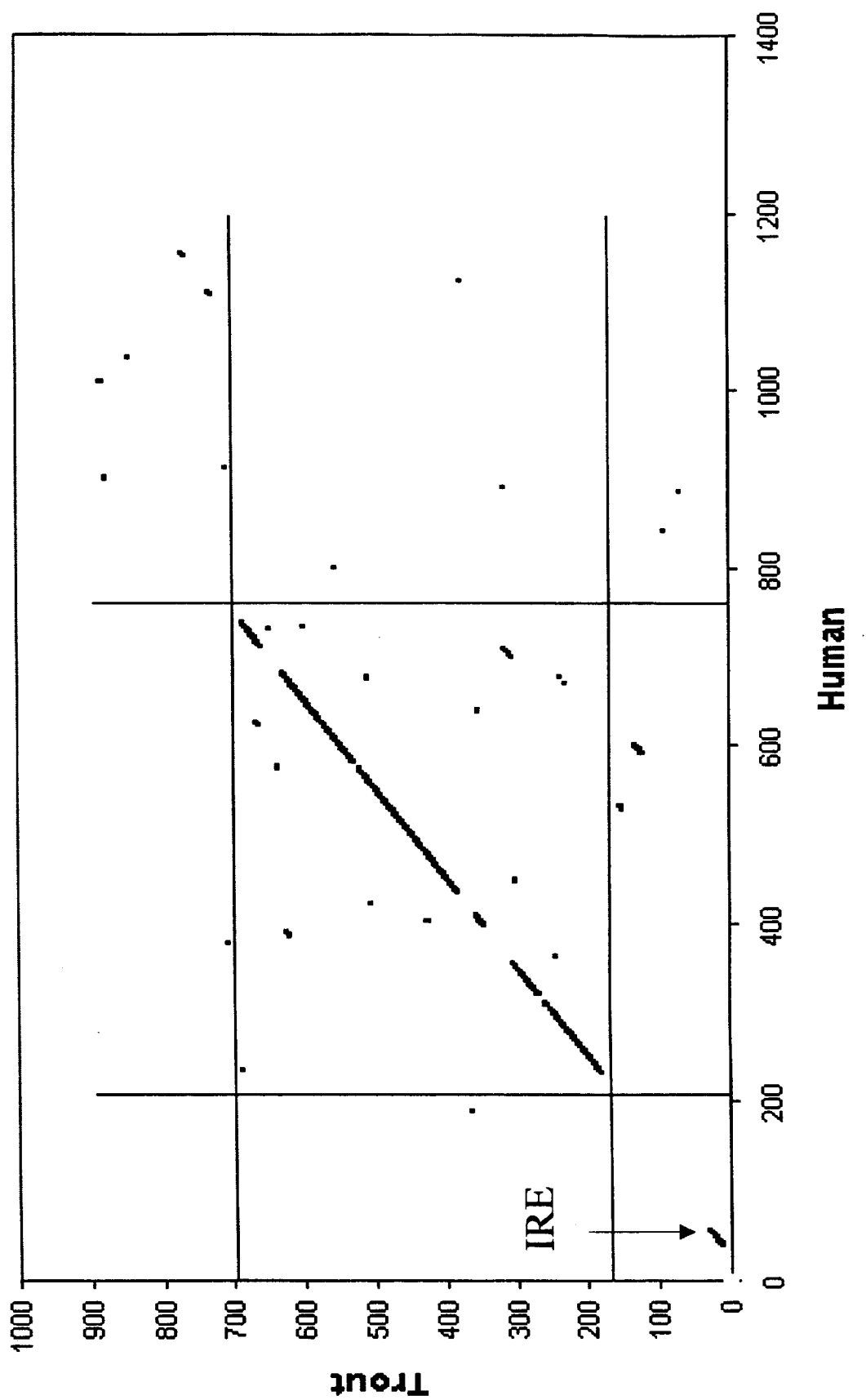
FIG. 11 is a representative scatter plot of an interspecies sequence comparison between human and trout for a ferritin RNA.
Figure 12:
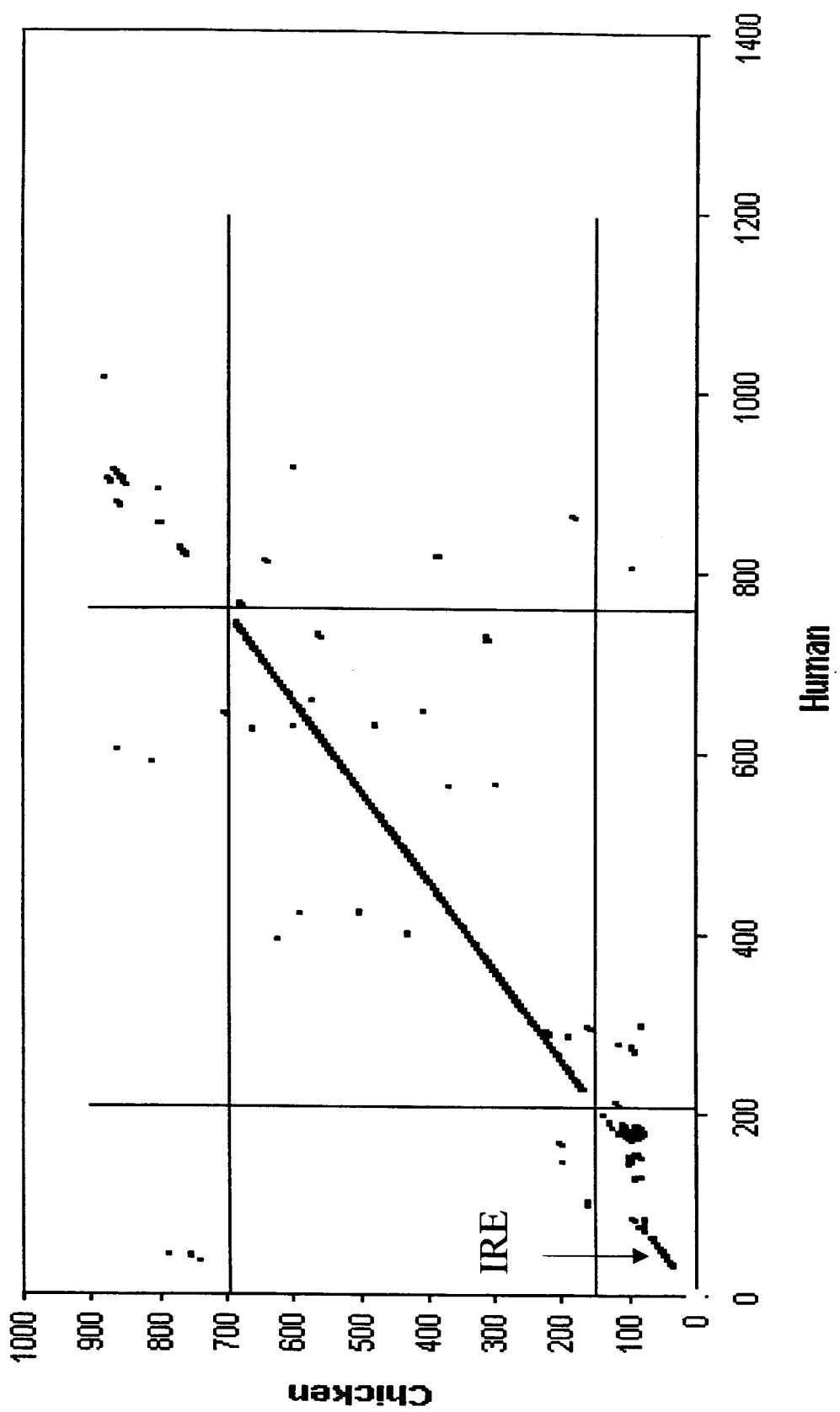
FIG. 12 is representative scatter plot of an interspecies sequence comparison between human and chicken for a ferritin RNA.

When the human mRNA and mouse mRNA sequences for ferritin, which each contain an IRE in the 5'-UTR, are analyzed in this manner, a plot showing the regions of sequence similarity is produced, as shown in FIG. 5. Pairwise analysis of the human and mouse ferritin mRNA sequences illustrate several important aspects of this type of analysis. Regions of each mRNA that encode the amino acid sequence have the highest degree of similarity, while the untranslated regions are less similar. In FIG. 5, the location of the IRE is indicated. In both the human and mouse ferritin mRNAs the IREs are located in the extreme 5' end of each mRNA. This demonstrates an important point—the sequence conservation in the region of the IRE structure does not stand out against the background of sequence similarity between the human and mouse ferritin sequences. In contrast, in the comparison of human and trout (FIG. 11) or human and chicken (FIG. 12) ferritin mRNAs, the IREs can be immediately identified. This is because the sequence of the UTRs between human and trout or human and chicken are separated by greater evolutionarily distance than human and mouse, which is logical in view of the evolutionary distance that separates humans from birds and fish compared with other mammals. Comparing the human sequence to that of birds and fish is informative because the natural drift due to evolution has allowed many sequence changes in the UTRs. However, the IRE sequences are more constrained because they form an important structure. Thus, they stand out better and can be more readily identified.

The same principle applies when comparing the trout and chicken ferritin sequences to each other. While both are separated from humans by hundreds of millions of years of evolution, they are also well separated from each other. This illustrates another important tactic used in the present invention—comparison of two non-human RNA sequences can be used to find a regulatory RNA structure without having the actual human sequence. The non-human comparison work can actually direct one skilled in the art where to look to find a human counterpart as a potential drug target.

Evolutionary distances can be used to decide which sequences not to compare as well as which to compare. As with the human and mouse, comparison of trout and salmon are less informative because the species are too close and the IRE does not stand out above the UTR background. Comparison of human and Drosophia ferritin mRNA sequences fail to find the IREs in either species, even though they are present. This is because the sequence of the IREs between humans and Drosophila have diverged even though the structure is conserved. However, if the Drosophila and mosquito ferritin mRNAs are compared, the IREs are identified, again illustrating that the human sequence need not be in hand to identify a regulatory element relevant to drug discovery in humans.

The software used in the present invention makes the decision whether or not to compare sequences pairwise using a lookup table based upon the evolutionary distances between species. An example of a small lookup table using the examples described above is shown in FIG. 13. The lookup table in the present invention includes all species that have sequences deposited in GenBank. Q-Compare in conjunction with CompareOverWins decides which sequences to compare pairwise.

5. Identification Of Secondary Structure

Sets of sequences that show evidence of conservation in orthologs and paralogs or other related genes are analyzed for the ability to form internal structure. This is accomplished by analyzing each sequence in a matrix where the seqeunce is plotted 5' to 3' on the X axis and its reverse complement is plotted 5' to 3' on the Y axis, such as in, for example, self-complementary analysis. Matches that correspond to potential intramolecular base pairs are scored according to a table of values. When the human ferritin IRE sequence is analyzed in this fashion, the diagonals indicate potential self-complementary regions. Each of the 13 IRE sequences described in this example were analyzed in the same fashion. While each of the sequences can form a variety of different structures, the structure most likely to occur is one common to all the sequences. By superimposing the plots of all 13 individual sequences (see, FIG. 8), the potential structure common to all the sequences is deduced.

What is claimed is:

1. A method of identifying molecular interaction sites in a target nucleic acid comprising:

comparing the nucleotide sequence of said target nucleic acid with the nucleotide sequences of a plurality of nucleic acids from different taxonomic species;

identifying at least one sequence region which is conserved among said plurality of nucleic acids and said target nucleic acid;

determining whether said conserved region has secondary structure; and for said conserved region having secondary structure, identifying said secondary structure.

2. The method of claim 1 further comprising identifying at least one structural motif for said conserved region having secondary structure.

3. The method of claim 2 further comprising constructing a set of descriptor elements for said structural motif.

4. The method of claim 3 further comprising identifying further nucleic acids having secondary structures corresponding to said descriptor elements.

5. The method of claim 1 wherein said target nucleic acid is present in a eukaryotic cell.

6. The method of claim 5 wherein said target nucleic acid is selected from the group consisting of mRNA, pre-mRNA, tRNA, rRNA, and snRNA.

7. The method of claim 1 wherein said target nucleic acid is present in a prokaryotic cell.

8. The method of claim 7 wherein said target nucleic acid is RNA.

9. The method of claim 7 wherein said target nucleic acid is bacterial.

10. The method of claim 7 wherein said target nucleic acid is viral.

11. The method of claim 7 wherein said target nucleic acid is from a parasite.

12. The method of claim 1 wherein at least some nucleic acid sequence information is derived from a genetic database.

13. The method of claim 1 wherein said nucleotide sequence of said target nucleic acid is determined by assembling a plurality of expressed sequence tags.

14. The method of claim 1 further comprising comparing said target nucleic acid to paralogous nucleic acids.

15. The method of claim 1 wherein said plurality of nucleic acids from different taxonomic species is obtained by performing a sequence similarity search, an ortholog search, or a combination thereof.

16. The method of claim 1 wherein said plurality of nucleic acids from different taxonomic species is obtained by performing a sequence similarity search and constructing virtual transcripts.

17. The method of claim 1 wherein determining whether said conserved region has secondary structure is performed by self complementarity comparison, alignment and covariance analysis, secondary structure prediction, or a combination thereof.

18. The method of claim 17, wherein said secondary structure comprises at least one bulge, loop, stem, hairpin, knot, triple interact, cloverleaf, or helix.

19. The method of claim 2 wherein said structural motif is identified by performing self complementarity comparison, alignment and covariance analysis, secondary structure prediction, or a combination thereof.

20. The method of claim 3 wherein said set of descriptor elements is constructed using a descriptor database.

21. The method of claim 4 wherein said other nucleic acids having secondary structures corresponding to said descriptor elements are identified by searching at least one database, performing clustering and analysis, searching for orthologs, or a combination thereof.

\* \* \* \* \*